United States Patent
Ban et al.

(10) Patent No.: US 10,597,397 B2
(45) Date of Patent: Mar. 24, 2020

(54) ADENINE CONJUGATE COMPOUNDS AND THEIR USE AS VACCINE ADJUVANTS

(71) Applicants: Sumitomo Dainippon Pharma Co., Ltd., Osaka (JP); AstraZeneca Aktiebolag, Södertälje (SE)

(72) Inventors: Hitoshi Ban, Nishinomiya (JP); Yukihiro Nishio, Fujisawa (JP); Padma Malyala, Burlington, MA (US); Bilikallahalli K. Muralidhara, Novato, CA (US); Marcus Wong, San Jose, CA (US)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 15/763,982

(22) PCT Filed: Sep. 28, 2016

(86) PCT No.: PCT/JP2016/004375
§ 371 (c)(1),
(2) Date: Mar. 28, 2018

(87) PCT Pub. No.: WO2017/056494
PCT Pub. Date: Apr. 6, 2017

(65) Prior Publication Data
US 2018/0282334 A1  Oct. 4, 2018

Related U.S. Application Data

(60) Provisional application No. 62/234,481, filed on Sep. 29, 2015.

(51) Int. Cl.
| | | |
|---|---|---|
| C07D 473/18 | (2006.01) | |
| A61K 31/522 | (2006.01) | |
| A61K 31/54 | (2006.01) | |
| A61K 31/59 | (2006.01) | |
| A61P 35/00 | (2006.01) | |
| C07D 473/34 | (2006.01) | |
| A61K 47/54 | (2017.01) | |
| A61K 47/69 | (2017.01) | |
| A61K 39/12 | (2006.01) | |
| A61K 39/39 | (2006.01) | |
| A61K 39/00 | (2006.01) | |

(52) U.S. Cl.
CPC .......... *C07D 473/18* (2013.01); *A61K 31/522* (2013.01); *A61K 39/0011* (2013.01); *A61K 39/12* (2013.01); *A61K 39/39* (2013.01); *A61K 47/54* (2017.08); *A61K 47/6907* (2017.08); *A61P 35/00* (2018.01); *C07D 473/34* (2013.01); *A61K 2039/55511* (2013.01); *A61K 2039/55566* (2013.01); *C12N 2710/16134* (2013.01); *C12N 2710/16634* (2013.01)

(58) Field of Classification Search
CPC ...... C07D 473/34; A61K 47/54; A61K 47/59; A61K 31/522; A61P 35/00
USPC ........................... 544/265; 514/263.1, 263.2
See application file for complete search history.

(56) References Cited

U.S. PATENT DOCUMENTS

| | | | |
|---|---|---|---|
| 4,689,338 | A | 8/1987 | Gerster |
| 6,329,381 | B1 | 12/2001 | Kurimoto et al. |
| 2007/0037832 | A1 | 2/2007 | Isobe et al. |
| 2010/0093998 | A1 | 4/2010 | Isobe et al. |
| 2018/0282334 | A1 * | 10/2018 | Ban ...................... A61K 31/522 |

FOREIGN PATENT DOCUMENTS

| | | |
|---|---|---|
| EP | 2133353 | 12/2009 |
| WO | WO 1999/28321 | 6/1999 |
| WO | WO 2002/85905 | 10/2002 |

(Continued)

OTHER PUBLICATIONS

Abdel-Magid et al., "Reductive Amination of Aldehydes and Ketones with Sodium Triacetoxyborohydride. Studies on Direct and Indirect Reductive Amination Procedures(1).", J. Org. Chem. 61, 3849, 1996.
Bakker et al., "Melanocyte Lineage-specific Antigen gp100 Is Recognized by Melanoma-derived Tumor-infiltrating Lymphocytes", J. Exp. Med., 179: 1005-1009, 1994.
Berman et al., "Protection from genital herpes simplex virus type 2 infection by vaccination with cloned type 1 glycoprotein D", Science 227: 1490-1492, 1985.
Bettinotti et al., "Clinical and immunological evaluation of patients with metastatic melanoma undergoing immunization with the HLA Cw*0702 associated epitope MAGE A12:170-178", Int. J. Cancer 105: 210, 2003.

(Continued)

*Primary Examiner* — Venkataraman Balasubramanian
(74) *Attorney, Agent, or Firm* — Fish & Richardson P.C.

(57) ABSTRACT

The present specification relates to adenine conjugate compounds represented by the formula (1), wherein A, $L^1$, $L^2$, $X^1$, $R^1$, $R^2$, $R^3$, and m are as defined herein, or their pharmaceutically acceptable salts. Compounds of formula (1) have immunostimulating properties and may therefore be useful in therapy, for example as vaccine adjuvants. The present specification also relates to a process for preparing adenine conjugate compounds and pharmaceutically acceptable salts thereof, and to pharmaceutical compositions comprising adenine conjugate compounds and their pharmaceutically acceptable salts.

(1)

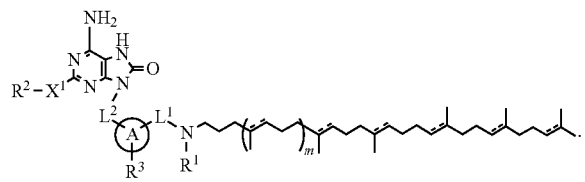

26 Claims, 11 Drawing Sheets

(56) References Cited

FOREIGN PATENT DOCUMENTS

| WO | WO 2005/001022 | 1/2005 |
| WO | WO 2005/018555 | 3/2005 |
| WO | WO 2007/034817 | 3/2007 |
| WO | WO 2008/114817 | 9/2008 |
| WO | WO 2010/048520 | 4/2010 |
| WO | WO 2010/093436 | 8/2010 |
| WO | WO 2011/017611 | 2/2011 |
| WO | WO 2011/139348 | 11/2011 |
| WO | WO 2012/011606 | 1/2012 |
| WO | WO 2012/024284 | 2/2012 |

OTHER PUBLICATIONS

Birchard et al., "The tyrosinase gene codes for an antigen recognized by autologous cytolytic T lymphocytes on HLA-A2 melanomas.", J. Exp. Med., 178, 489-495, 1993.
C.B. Fox, "Squalene Emulsions for Parenteral Vaccine and Drug Delivery", Molecules, 14, 3286-3312, 2009.
Ceruti e al., "Synthesis and biological activity of new Iodoacetamide derivatives on mutants of squalene hopene cyclase", Lipids 40, 729-735, 2005.
Cormier et al., "Enhancement of Cellular Immunity in Melanoma Patients Immunized with a Peptide from MART-1/Melan A", Cancer J. Sci. Am. 3: 37-44, 1997.
Correale et al., "In vitro generation of human cytotoxic T lymphocytes specific for peptides derived from prostate-specific antigen.", J. Natl. Cancer. Inst., 89: 293-300, 1997.
Coulie et al., "Cytolytic T-cell responses of cancer patients vaccinated with a MAGE antigen.", Immunol. Rev. 188: 33-42, 2002.
Fisk et al., "Identification of an immunodominant peptide of HER-2/neu protooncogene recognized by ovarian tumor-specific cytotoxic T lymphocyte lines.", J. Exp. Med., 181, 2109-2117, 1995.
Frey et al., "Effects of Antigen Dose and Immunization Regimens on Antibody Responses to a Cytomegalovirus Glycoprotein B Subunit Vaccine", Infect Dis. 180: 1700-1703, 1999.
Galandrini et al., "CD16-mediated p21 ~ Activation Is Associated with Shc and p36 Tyrosine Phosphorylation and Their Binding with Grb2 in Human Natural Killer Cells", J. Exp. Med., 183: 179-186, 1996.
Gaugler et al., "Human gene MAGE-3 codes for an antigen recognized on a melanoma by autologous cytolytic T lymphocytes.", J. Exp. Med., 179, 921-930, 1994.
Gonczol et al., "Development of a cytomegalovirus vaccine: lessons from recent clinical trials", Exp. Opin. Biol. Ther. 1: 401-412, 2001.
International Preliminary Report on Patentability in International Application No. PCT/JP2016/004375, dated Apr. 3, 2018, 9 pages.
International Search Report in International Application No. PCT/JP2016/004375, dated Dec. 13, 2016, 3 pages.
Iwasaki et al., "Toll-like receptor control of the adaptive immune responses", Nat. Immunol. 2004, vol. 5, 987-995, 2004.
Jager et al., "Granulocyte macrophage colony stimulating factor enhances immune responses to melanoma associated peptides in vivo", Int. J. Cancer 67: 54-62, 1996.
Kawakami et al., "Cloning of the gene coding for a shared human melanoma antigen recognized by autologous T cells infiltrating into tumor.", Proc. Natl. Acad. Sci. USA, 91, 3515-3519, 1994.
Knutson et al., "Immunization with a HER-2/neu helper peptide vaccine generates HER-2/neu CD8 T-cell immunity in cancer patients", J. Clin. Invest. 107: 477-484, 2001.
O'Hagan et al., "The mechanism of action of MF59—An innately attractive adjuvant formulation", Vaccine 30, 4341-4348, 2012.

Oka et al., "Induction of WT1 (Wilms' tumor gene)-specific cytotoxic T lymphocytes by WT1 peptide vaccine and the resultant cancer regression", Proc. Natl. Acad. Sci. USA, 101: 13885-13890, 2004.
Othman et al., "Synthesis and physicochemical characterization of new squalenoyl amphiphilic gadolinium complexes as nanoparticle contrast agents.", Org. Biomol. Chem. 9, 4367-4386, 2011.
Ott et al., "The Adjuvant MF59: A 10-Year Perspective", Methods in Molecular Medicine, 42, 211-228, 2000.
Phan et al., "Cancer regression and autoimmunity induced by cytotoxic T lymphocyte-associated antigen 4 blockade in patients with metastatic melanoma.", Proc. Natl. Acad. Sci. USA 100: 8372-8377, 2003.
Ressing et al., "Human CTL epitopes encoded by human papillomavirus type 16 E6 and E7 identified through in vivo and in vitro immunogenicity studies of HLA-A*0201-binding peptides.", J. Immunol., 154: 5934-5943, 1995.
Rosa et al., "Preclinical development of an adjuvant-free peptide vaccine with activity against CMV pp65 in HLA transgenic mice", Blood 100: 3681-3689, 2002.
Rosenberg et al., "Immunologic and therapeutic evaluation of a synthetic peptide vaccine for the treatment of patients with metastatic melanoma.", Nat. Med. 4: 321-327, 1998.
Ross, "Comments on the article "Persistent confusion of total entropy and chemical system entropy in chemical thermodynamics" [(1996) Proc. Natl. Acad. Sci. USA 93, 7452-7453]", Proc. Natl. Acad. Sci. USA, 93, 14314, 1996.
Scheibenbogen et al., "Phase 2 Trial of Vaccination With Tyrosinase Peptides and Granulocyte-Macrophage Colony-Stimulating Factor in Patients With Metastatic Melanom", J. Immunother. 23: 275-281, 2000.
Sen et al., "Trisnorsqualene alcohol, a potent inhibitor of vertebrate squalene epoxidase", J. Am. Chem. Soc. 111, 1508-1510, 1989.
Smirnov et al., "Vaccine adjuvant activity of 3M-052: An imidazoquinoline designed for local activity without systemic cytokine induction", Vaccine 29, 5434-5442, 2011.
Smith et al., "Adjuvant Immunization of HLA-A2-Positive Melanoma Patients With a Modified gp100 Peptide Induces Peptide-Specific CD8+ T-Cell Responses", J. Clin. Oncol. 21: 1562, 2003.
Steinhagen et al., "TLR-based immune adjuvants", Vaccine 29, 3341-3335, 2011.
Stuber et al., "HLA-A0201 and HLA-B7 binding peptides in the EBV-encoded EBNA-1, EBNA-2 and BZLF-1 proteins detected in the MHC class I stabilization assay. Low proportion of binding motifs for several HLA class I alleles in EBNA-1.", Int. Immunol., 7: 653-663, 1995.
Tomai et al., "Resiquimod and other immune response modifiers as vaccine adjuvants", Exp. Rev. Vaccine, 6, 835-847, 2007.
Tsang et al., "Generation of Human Cytotoxic T Cells Specific for Human Carcinoembryonic Antigen Epitopes From Patients Immunized With Recombinant Vaccinia—CEA Vaccine ", J. Natl. Cancer. Inst., 87: 982-990, 1995.
Van Der Bruggen et al., "A Gene Encoding an Antigen Recognized by Cytolytic T Lymphocytes on a Human Melanoma", Science, 254: 1643-1647 1991.
Van Driel et al., "Vaccination with HPV16 peptides of patients with advanced cervical carcinoma: clinical evaluation of a phase I-II trial", Eur. J. Cancer 35: 946, 1999.
Wolfel et al., "A p16INK4a—Insensitive CDK4 Mutant Targeted by Cytolytic T Lymphocytes in a Human Melanoma", Science, 269: 1281-1285, 1995.
Ross, "Comments on the article "Persistent confusion of total entropy and chemical system entropy in chemical thermodynamics" [(1996) Proc. Natl. Acad. Sci. USA 93, 7452-7453]", Proc. Natl. Acad. Sci. USA, 93: p. 14704, 1996.

* cited by examiner

[Fig. 1]
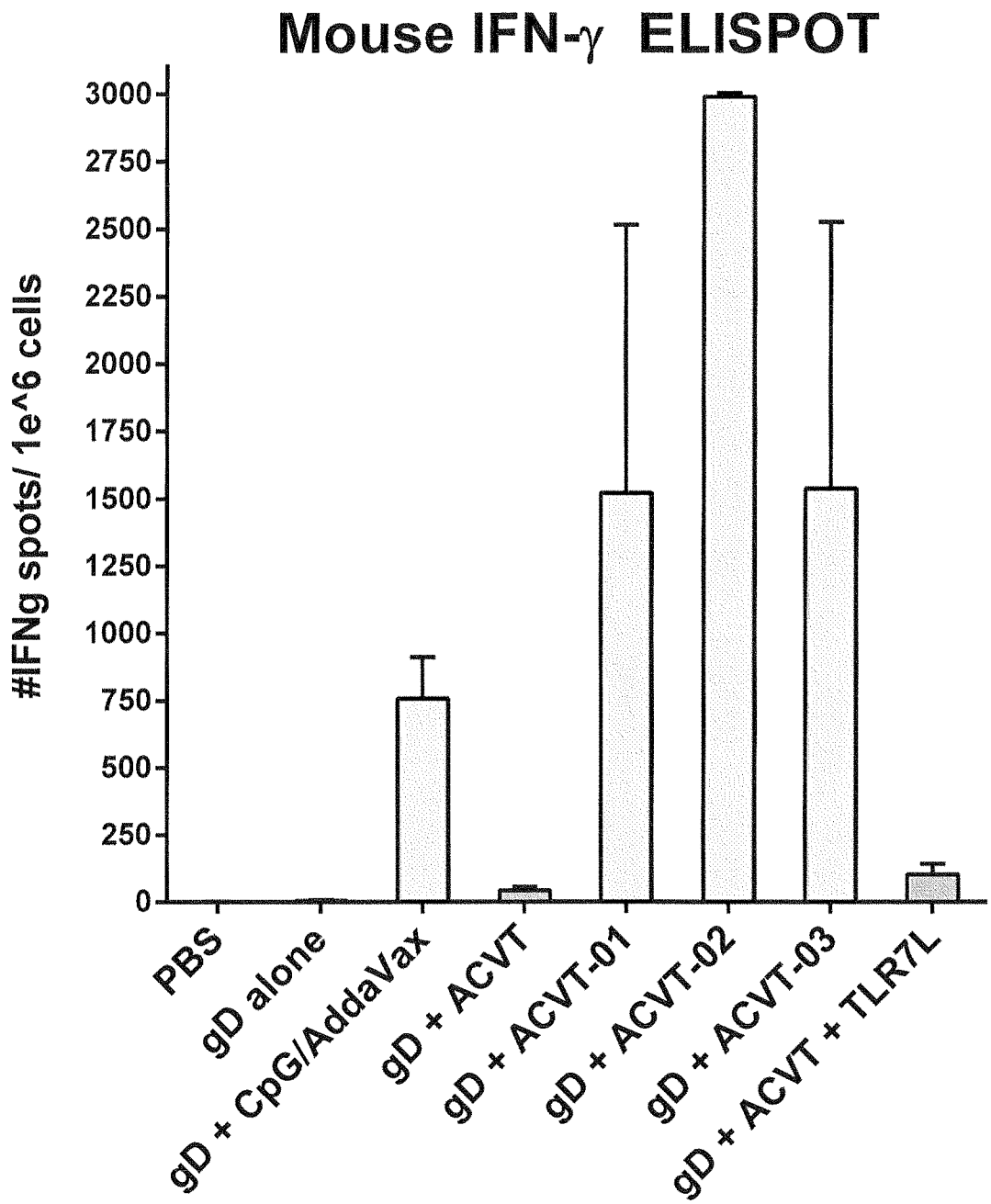

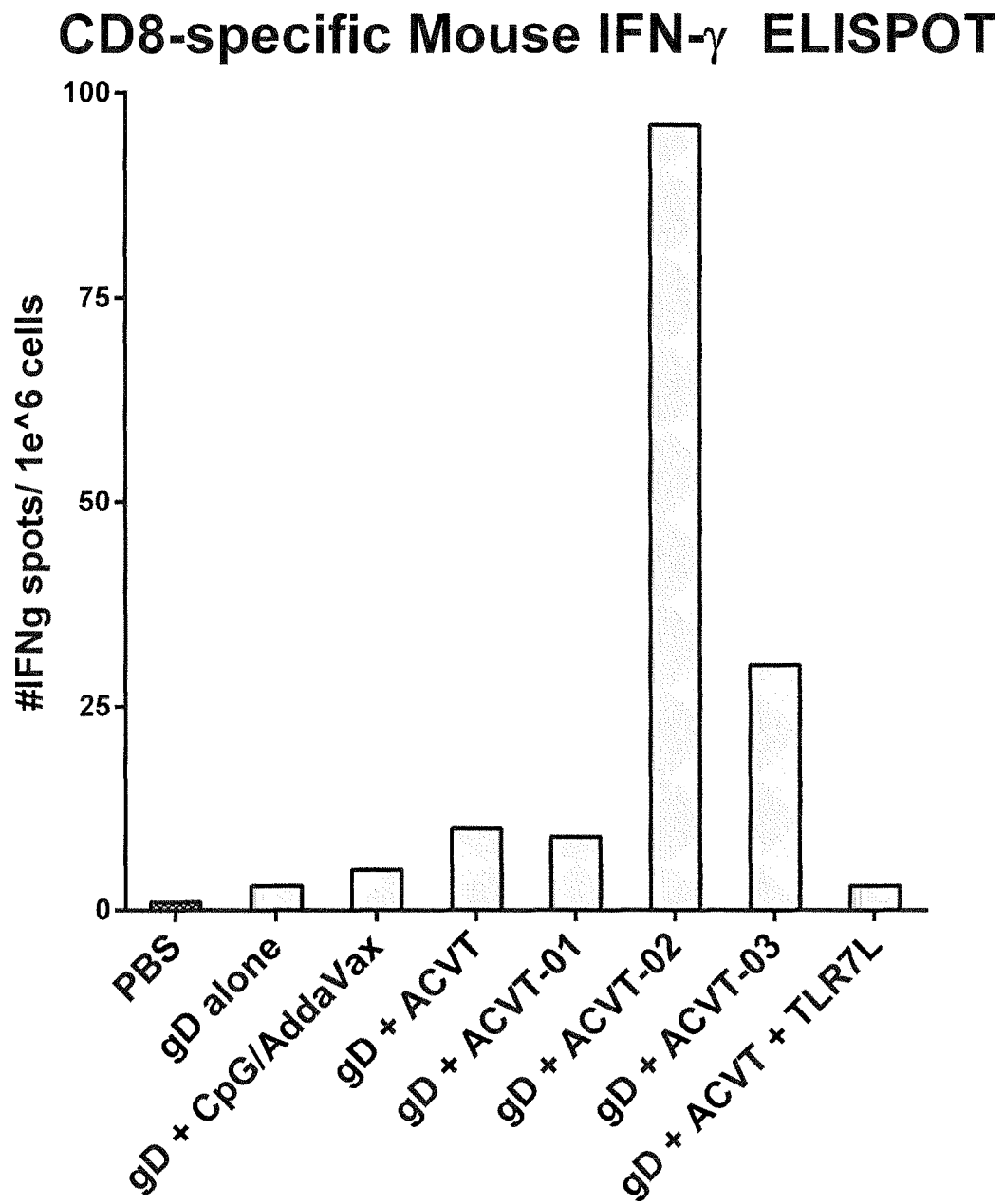
[Fig. 2]

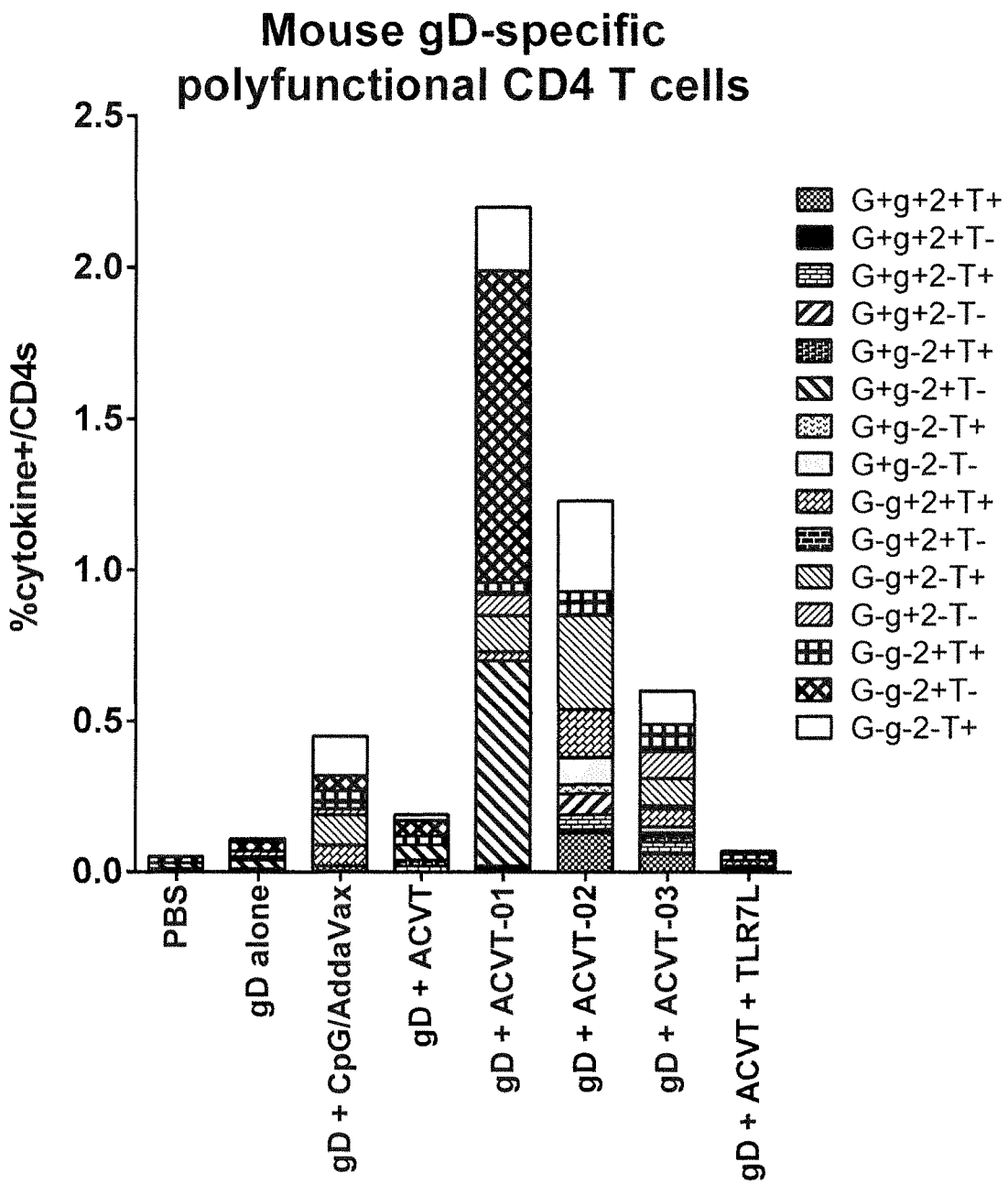
[Fig. 3]

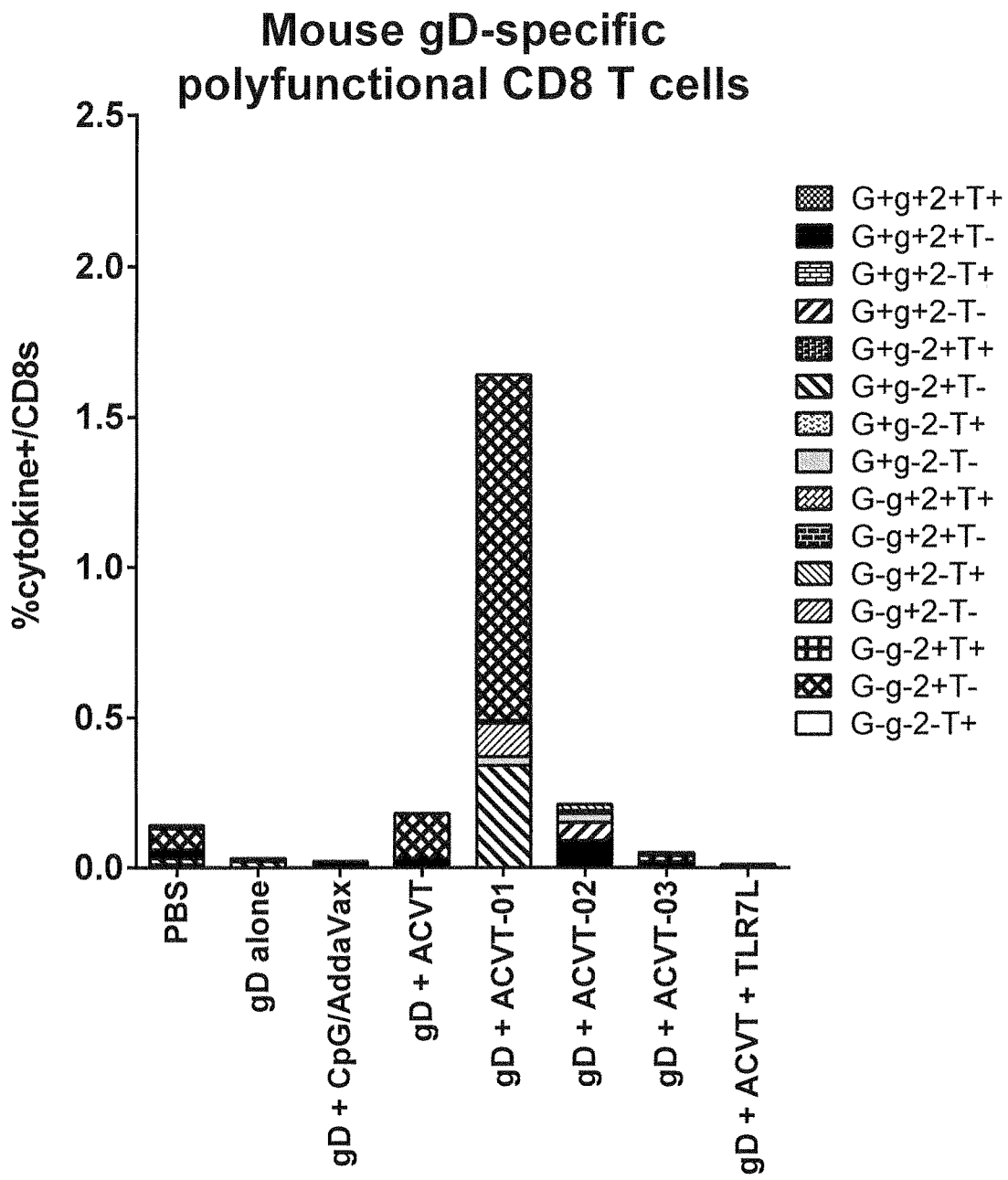
[Fig. 4]

[Fig. 5]
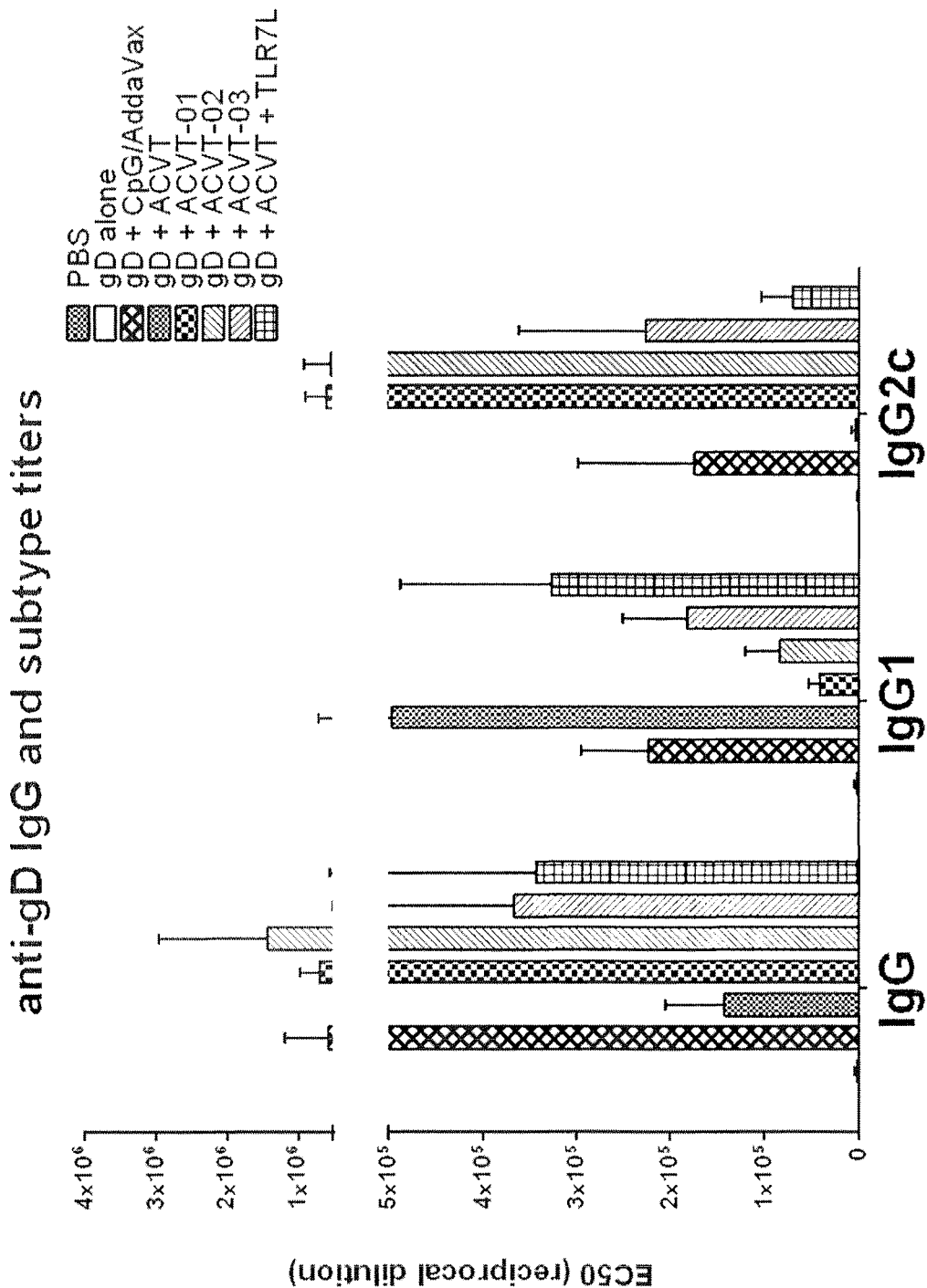

[Fig. 6]
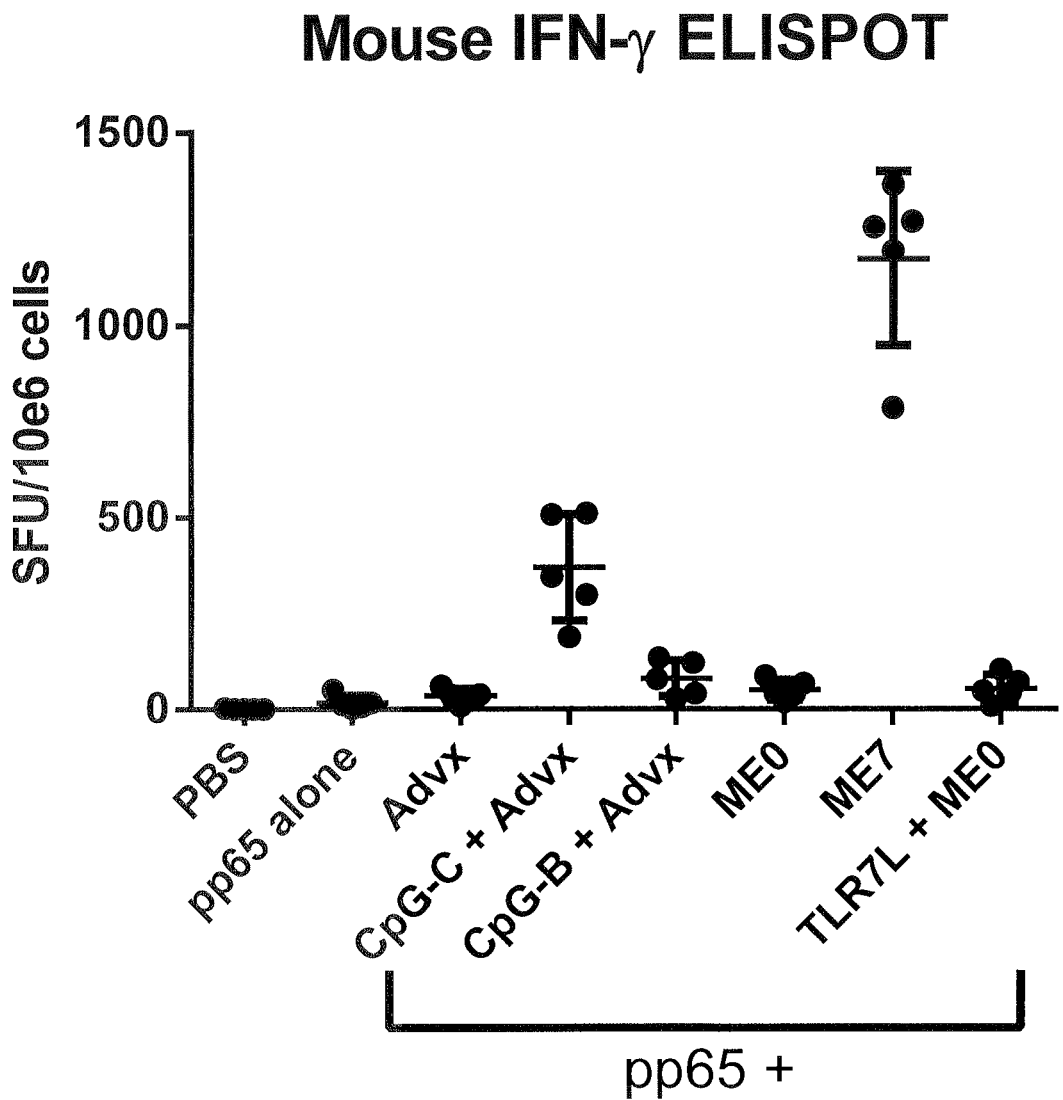

[Fig. 7]
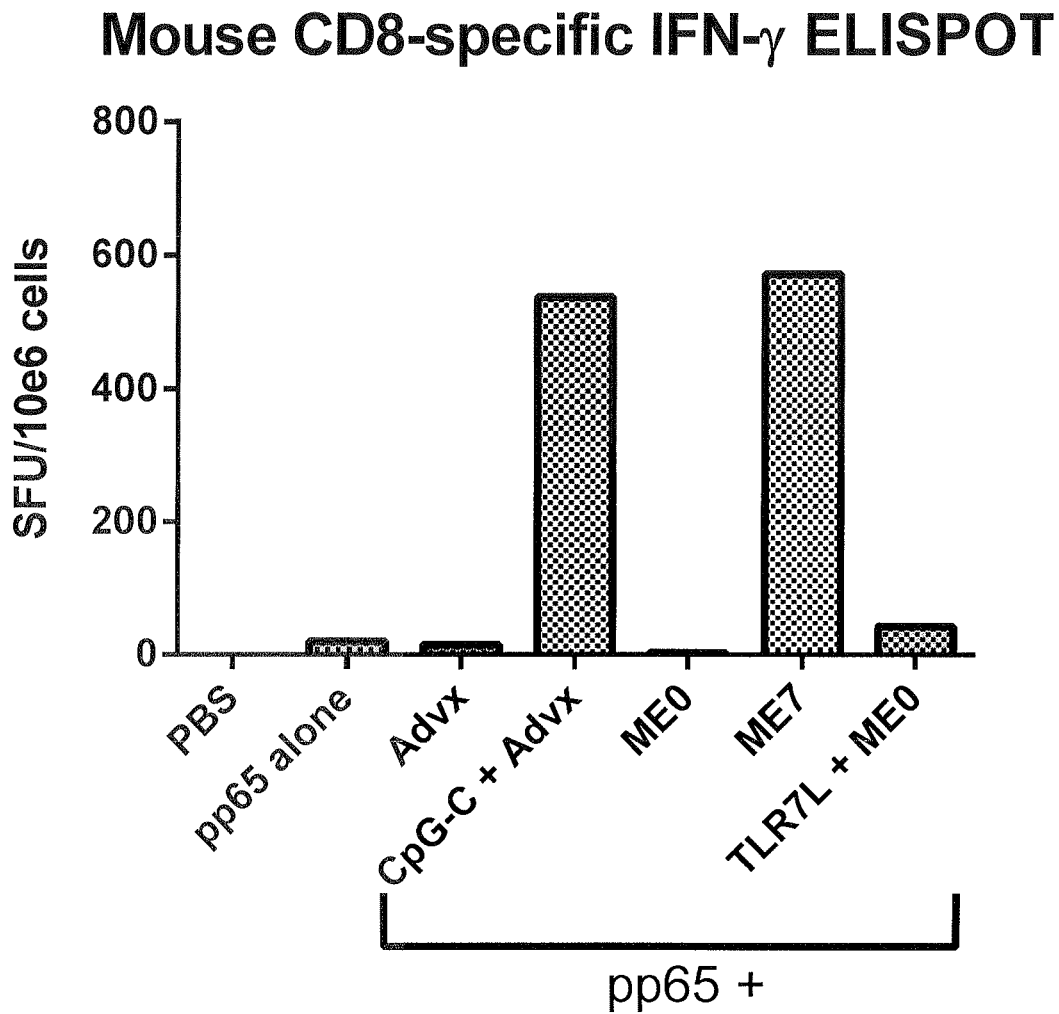

[Fig. 8]
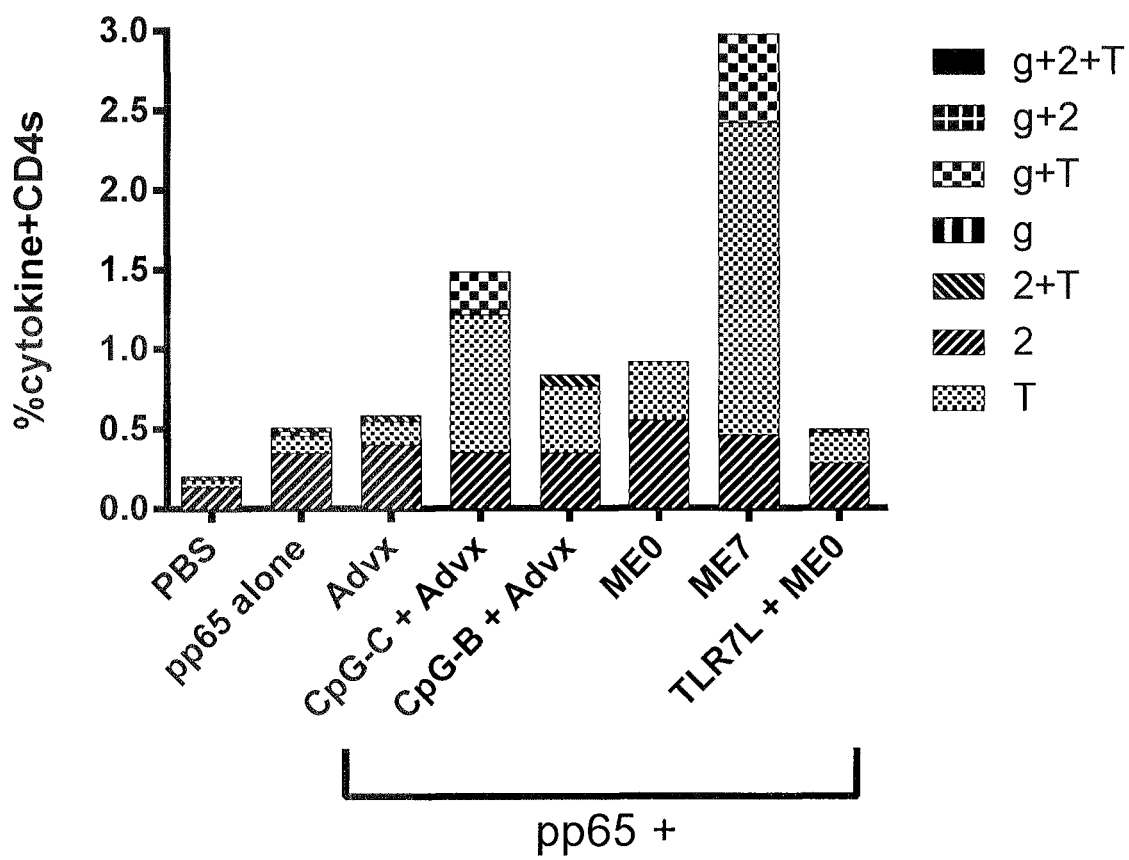

[Fig. 9]
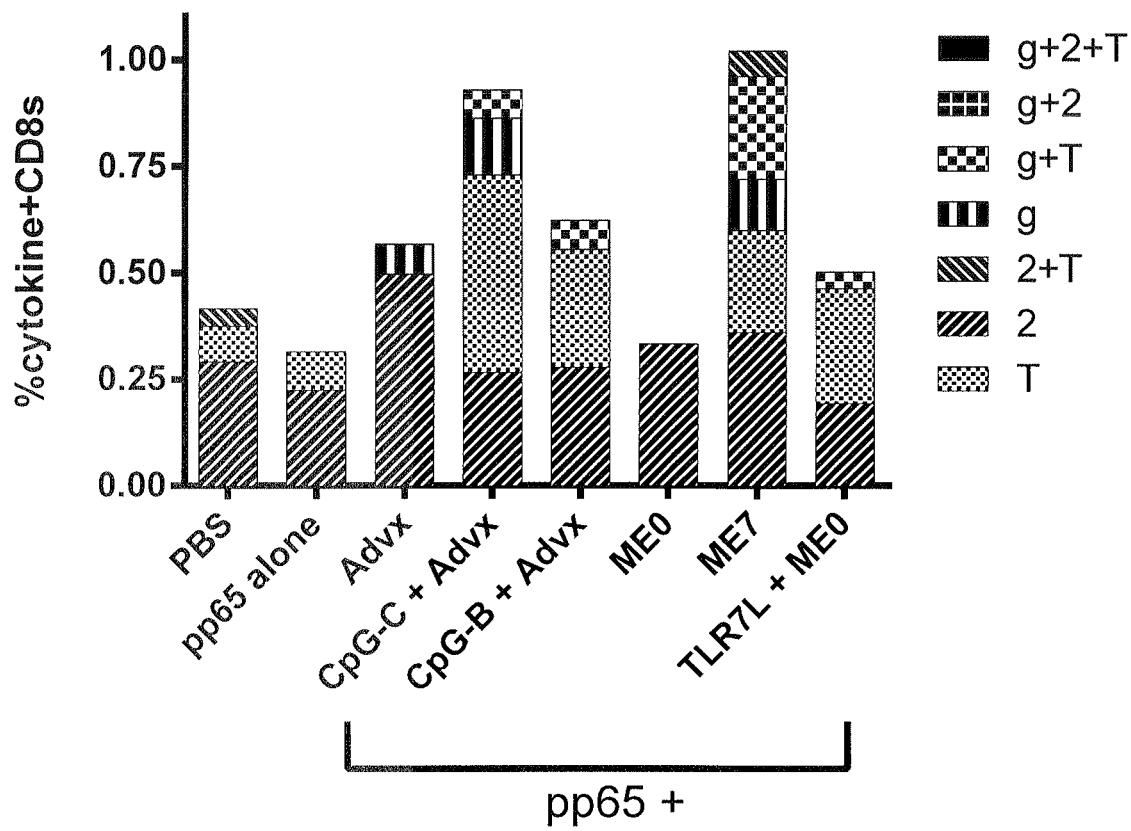

[Fig. 10]
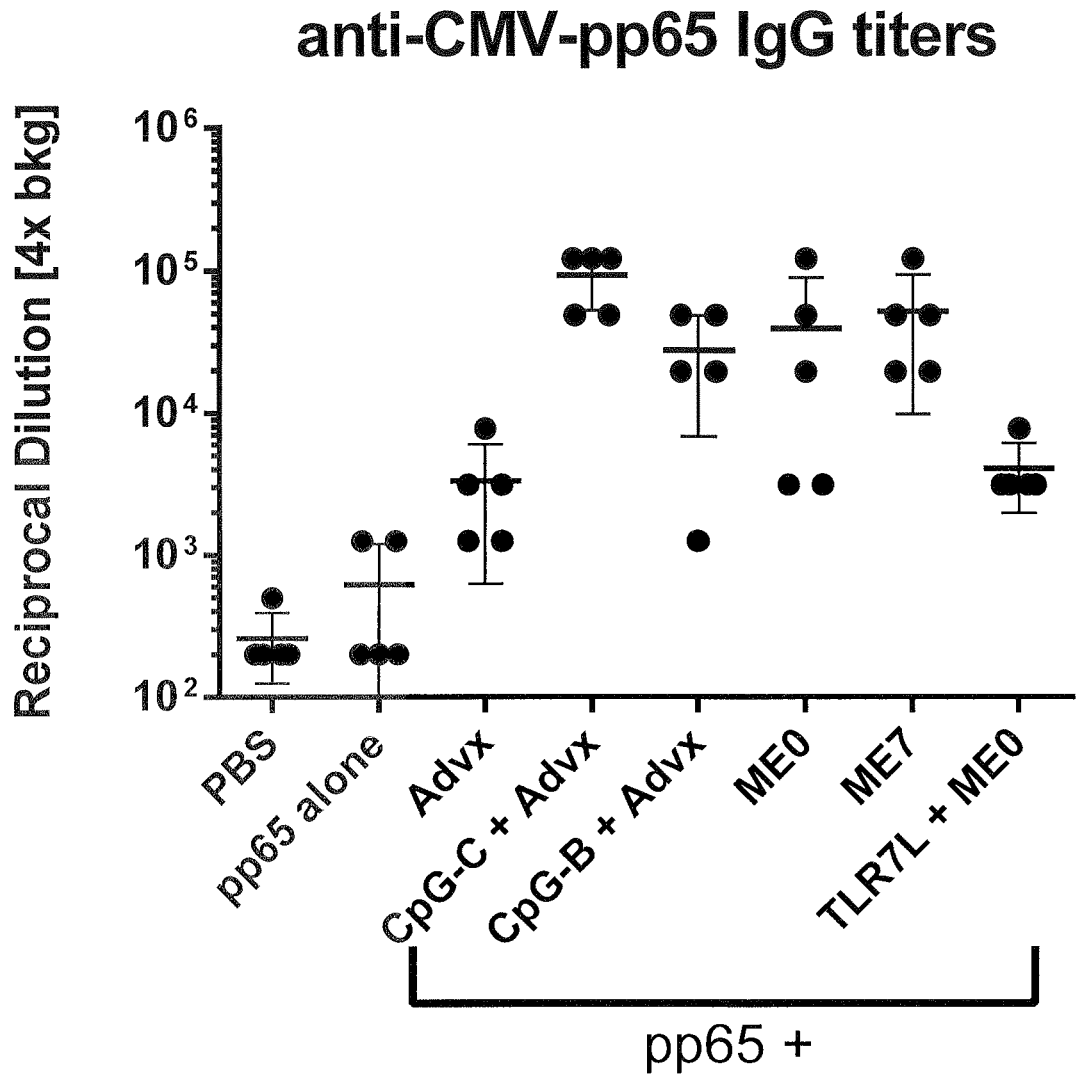

[Fig. 11]
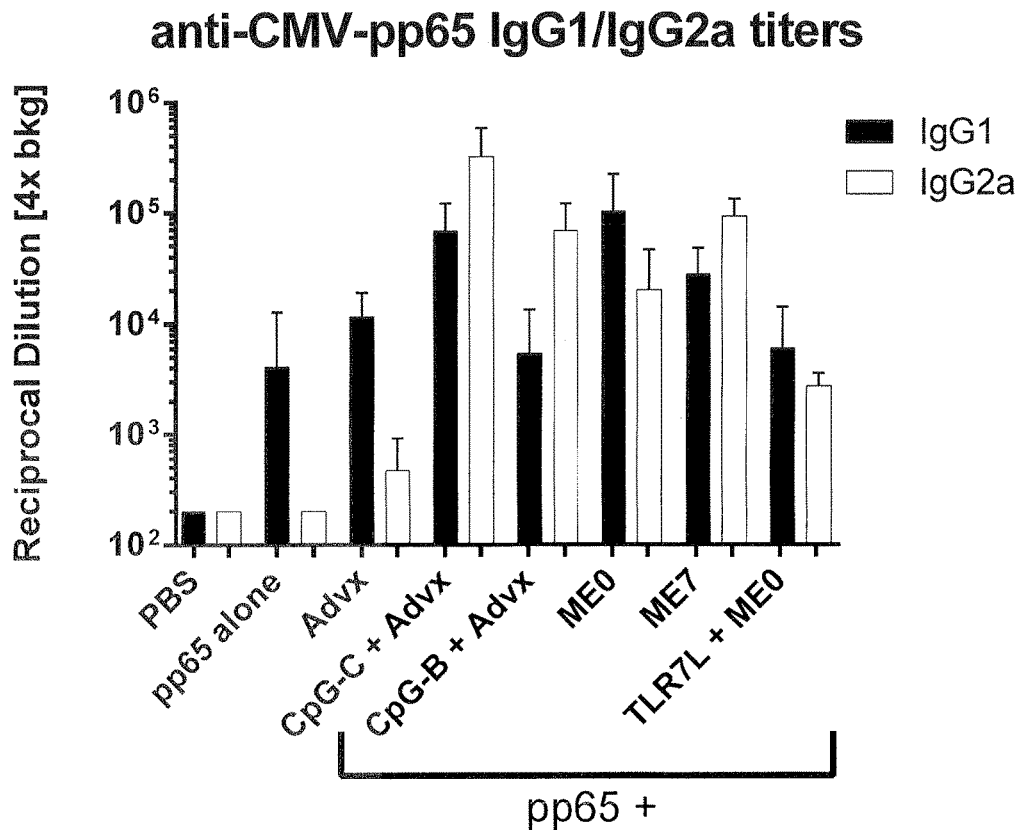
[Fig. 12]
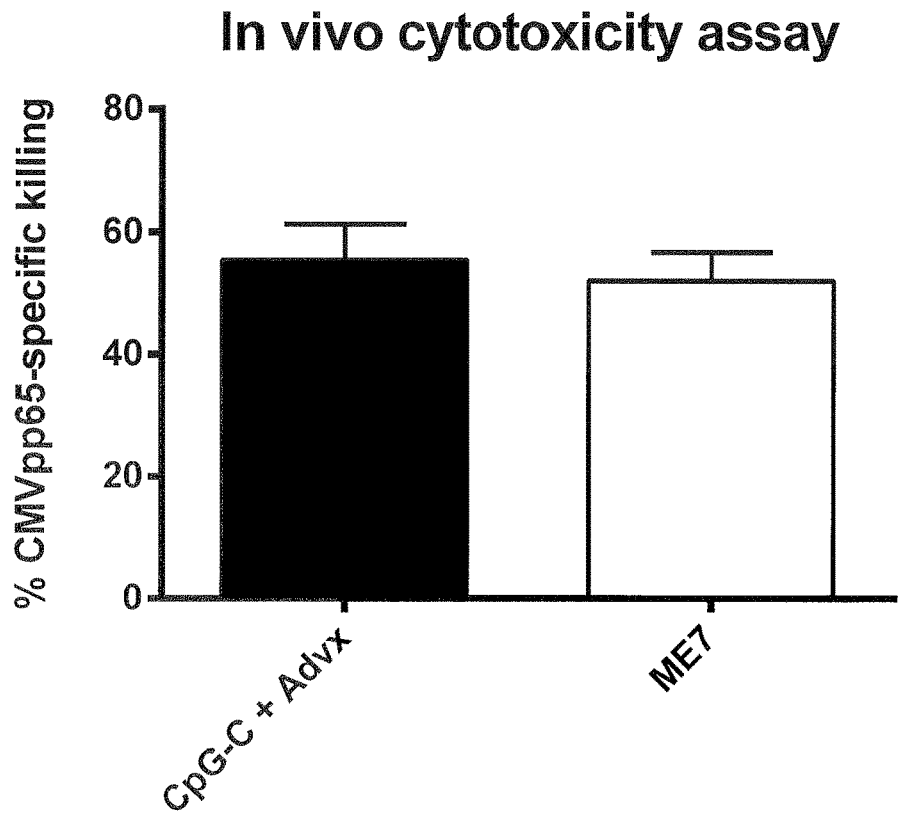

ADENINE CONJUGATE COMPOUNDS AND THEIR USE AS VACCINE ADJUVANTS

FIELD

The present specification relates to adenine conjugate compounds and pharmaceutically acceptable salts thereof. These compounds have immunostimulating properties and may therefore be useful in therapy, for example as vaccine adjuvants. The present specification also relates to a process for preparing adenine conjugate compounds and pharmaceutically acceptable salts thereof, and to pharmaceutical compositions comprising adenine conjugate compounds and their pharmaceutically acceptable salts.

BACKGROUND

A vaccine comprising a protein or its partial peptide derived from a microorganism (a "subunit vaccine") is advantageous since it can be conveniently prepared through chemical synthesis or recombinant techniques and may have superior safety to live vaccines or inactivated vaccines. However, such subunit vaccines tend to exhibit a lower immunostimulating activity than live vaccine or inactivated vaccine alternatives. In order to improve the immunostimulating activity of subunit vaccines, they may be administered with a vaccine adjuvant in combination with an antigen.

A vaccine adjuvant is an additive enhancing the mammalian immune response and/or cellular immunity response to an antigen. Alum, saponin and the like are used as vaccine adjuvants.

Recently, it has been found that Toll-like Receptors ("TLRs") play an important role in activating innate immunity, which is one of the common host defense mechanisms against microorganisms. Immune modifying agents such as monophosphoryl lipid A (MPL), CPG ODN and the like can exhibit immunostimulating activity via TLRs.

Amongst the 13 known TLRs identified in human beings several are associated with the recognition of bacterial components (TLRs 1, 2, 4, 5, and 6), viral RNA (TLRs 3, 7, and 8) or unmethylated DNA (TLR 9) (see, Non-patent Reference 1).

It is known that TLR 7 and TLR 8 activators include low molecular weight mimics of the viral single-stranded RNA which is a natural ligand for the receptors in question. For example, synthetic compounds such as 8-oxoadenine compounds (see, Patent References 1, 2, and 3) and imidazoquinoline compounds (see, Patent Reference 4) which mimic viral RNA have been already reported to activate TLR 7 and/or TLR 8.

When TLR 7 and/or TLR 8 are activated, Th1 cells are induced via a TLR/MyD88-dependent signal transduction pathway to activate dendritic cells (DCs). Consequently, the expression of T cell co-stimulatory molecules (CD80, CD86, and CD40) is enhanced and inflammatory cytokines including interferon type I (particularly IFNα), IFNγ, TNFα, IL-6 or IL-12 are produced.

It is also known that TLR 7 and/or TLR 8 activators trigger B cells and further stimulate NK cells to promote IFNγ production as well as DC activation. These pathways are expected to contribute to vaccine adjuvant activity. Indeed, the adjuvant activity of TLR 7/TLR 8 activators such as Resiquimod and Imiquimod has already been reported (see, Non-patent References 2 and 3).

Nevertheless, it is desirable to develop a novel vaccine adjuvant to activate TLR 7 and/or TLR 8.

Squalene is an oily substance used as an ingredient in oil-in-water or water-in-oil emulsion formulations. It is known to enhance the immunostimulating activity of an antigen when used as a surfactant in water-in-oil or oil-in-water emulsions associated with an antigen. Indeed, squalene is used as a base substance of the known vaccine adjuvant MF59, which is useful as an influenza vaccine (see, Non-patent References 4, 5, and 6).

Complexes of TLR 7 and/or TLR8 activator and another substance are known. For example, a vaccine adjuvant prepared by covalently-binding a fatty acid and an imidazoquinoline compound has been reported to allow a TLR 7 activator to be localized in the target tissue, reducing the metabolism and toxicity of the TLR 7 activator (see, Patent References 5, 6, and 7, and Non-patent Reference 7) Furthermore, a complex of a fatty acid glyceride and an imidazoquinoline compound (see, Patent Reference 8), a complex of a fatty acid glyceride and an adenine compound (see, Patent Reference 9), and a complex of phospholipid and an adenine compound (see, Patent Reference 10) are known. A complex of a fatty acid glyceride and an adenine compound via polyethylene glycol has also been reported (see, Patent Reference 11).

However, no complexes of a TLR 7/8 activator and squalene have yet been reported.

CITATION LIST

Non Patent Literature

[NPL 1] Iwasaki, A., Nat. Immunol. 2004, 5, 987.
[NPL 2] Steinhagen, F. et al., Vaccine 2011, 29, 3341.
[NPL 3] M. A. Tomai et al, Exp. Rev. Vaccine, 6, 835.
[NPL 4] G. Ott et al. Methods in Molecular Medicine, 2000, 42, 211-228.
[NPL 5] D. T. O'Hagan et al. Vaccine 2012, 4341-4348.
[NPL 6] C. B. Fox, molecules 2009, 14, 3286.
[NPL 7] Smirnov, D. et al., Vaccine 2011, 29, 5434.

Patent Literature

[PTL 1] WO 99/28321
[PTL 2] WO 02/85905
[PTL 3] WO 2008/114817
[PTL 4] U.S. Pat. No. 4,689,338 B
[PTL 5] WO 2005/001022
[PTL 6] WO 2005/018555
[PTL 7] WO 2012/024284
[PTL 8] WO 2010/048520
[PTL 9] WO 2011/017611
[PTL 10] WO 2011/139348
[PTL 11] WO 2010/093436

SUMMARY

Technical Problem

The problem to be solved by the present specification is to provide novel compounds with properties useful in therapy, and in particular in vaccine adjuvant applications.

Solution to Problem

The present inventors have extensively studied the above problem and have prepared certain conjugate compounds comprising an adenine TLR 7 modulator bound to an oily substance via a spacer. As shown in the Industrial Applicability section, these conjugate compounds exhibit vaccine adjuvant activity which enhances the immunostimulating activity of an antigen substance. Surprisingly, the conjugate compounds of the specification also demonstrate more potent adjuvant activity than of each of the adenine compound and the oily substance alone. As such, the conjugate compounds of the specification have been found to solve the stated technical problem.

Many embodiments are detailed throughout the specification and will be apparent to a reader skilled in the art. The invention described by the specification is not to be interpreted as being limited to any particular embodiment(s) thereof. In brief, the present specification relates to the following embodiments.

[1] A compound represented by the formula (1) or its pharmaceutically acceptable salt:

[Chem.1]

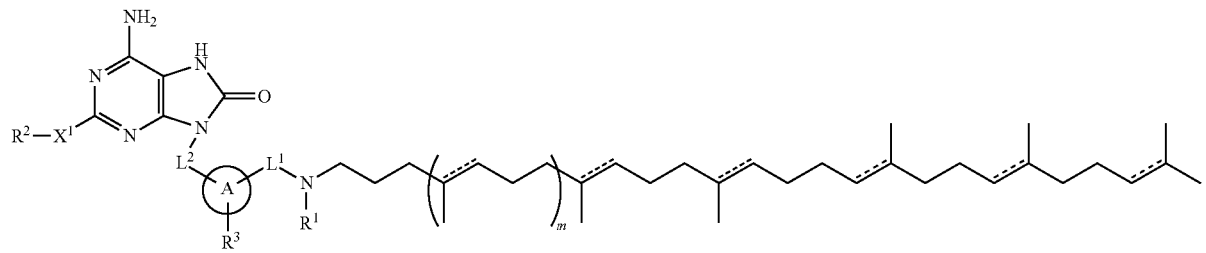

(1)

wherein
$L^1$ and $L^2$ are independently alkylene;
$R^1$ is hydrogen atom or alkyl;
$R^2$ is optionally substituted alkyl;
$R^3$ is hydrogen atom, halogen atom, alkyl or alkoxy;
$X^1$ is a single bond, oxygen atom, sulfur atom, SO, $SO_2$, $NR^4$ or $CONR^4$;
$R^4$ is hydrogen atom or alkyl;
A is monocyclic aromatic carbocycle, or 5- or 6-membered aromatic heterocycle which includes 1 to 4 heteroatoms selected from the group consisting of 1 to 4 nitrogen atoms, an oxygen atom and a sulfur atom;
m is 0 or 1; and
a bond described by
[Chem.2]
=====
independently represents a single bond or a double bond.

[2] The compound represented by the formula (1) according to [1] or its pharmaceutically acceptable salt, wherein
$L^1$ is $C_{1-4}$ alkylene;
$L^2$ is $C_{1-4}$ alkylene;
$R^1$ is hydrogen atom or $C_{1-4}$ alkyl;
$R^2$ is $C_{1-6}$ alkyl optionally substituted by 1 to 4 groups that may be the same or different selected from hydroxy, halogen atom, $C_{1-6}$ alkyl, $C_{1-6}$ haloalkyl, $C_{1-6}$ alkoxy, $C_{1-6}$ haloalkoxy, amino optionally substituted by one or two $C_{1-6}$ alkyl that may be the same or different, and carboxy;
$R^3$ is hydrogen atom, halogen atom, $C_{1-4}$ alkyl or $C_{1-4}$ alkoxy;
$X^1$ is single bond, oxygen atom, sulfur atom, SO, $SO_2$, $NR^4$ or $CONR^4$; and
$R^4$ is hydrogen atom or $C_{1-4}$ alkyl.

[3] The compound represented by the formula (1) according to [1] or [2], or its pharmaceutically acceptable salt, wherein $R^2$ is $C_{1-6}$ alkyl optionally substituted by 1 to 3 groups that may be the same or different selected from hydroxy, halogen atom, $C_{1-6}$ alkoxy and $C_{1-6}$ haloalkoxy.

[4] The compound represented by the formula (1) according to any one of [1] to [3], or its pharmaceutically acceptable salt, wherein A is benzene ring or pyridine ring.

[5] The compound represented by the formula (1) according to [4], or its pharmaceutically acceptable salt, wherein A is benzene ring.

[6] The compound represented by the formula (1) according to any one of [1] to [5], or its pharmaceutically acceptable salt, wherein $L^2$ is methylene.

[7] The compound represented by the formula (1) according to any one of [1] to [6], or its pharmaceutically acceptable salt, wherein $R^2$ is $C_{1-4}$ alkyl, $C_{1-4}$ hydroxy-alkyl or $C_{1-4}$ alkoxy-$C_{1-4}$ alkyl.

[8] The compound represented by the formula (1) according to any one of [1] to [7], or its pharmaceutically acceptable salt, wherein $L^1$ is $C_{1-3}$ alkylene, and $R^1$ is hydrogen atom or $C_{1-3}$ alkyl.

[9] The compound represented by the formula (1) according to any one of [1] to [8], or its pharmaceutically acceptable salt, wherein all of the bonds described by

[Chem.3]
===== represent a single bond, or all of the bonds described by

[Chem.4]
===== represent a double bond.

[10] The compound represented by the formula (1) according to any one of [1] to [9], or its pharmaceutically acceptable salt, wherein $R^1$ is hydrogen atom or methyl.

[11] The compound represented by the formula (1) according to [1], or its pharmaceutically acceptable salt, wherein $L^1$ is methylene;

$L^2$ is methylene;

$R^1$ is hydrogen atom or methyl;

$R^2$ is $C_{1-6}$ alkyl, $C_{1-3}$ alkoxy-$C_{2-4}$ alkyl or $C_{2-6}$ alkyl substituted by 1 to 4 hydroxy groups wherein two or more hydroxy groups are attached to different carbon atoms;

$R^3$ is hydrogen atom, $C_{1-3}$ alkyl, $C_{1-3}$ alkoxy or halogen atom;

$X^1$ is single bond, oxygen atom, $NR^4$ or $CONR^4$;

$R^4$ is hydrogen atom or $C_{1-3}$ alkyl;

A is benzene ring or pyridine ring; and
all of the bonds described by
[Chem.5]

represent a single bond, or all of the bonds described by
[Chem.6]

represent a double bond.

[12] A pharmaceutical composition comprising a compound represented by the formula (1) according to any one of [1] to [11], or its pharmaceutically acceptable salt.

[13] The pharmaceutical composition according to [12] where the pharmaceutical composition is an oil-in-water emulsion comprising squalene as an oil component, Span (Registered Trademark) 85 (Sorbitan Trioleate) and Poloxamer 188.

[14] The pharmaceutical composition according to [12] where the pharmaceutical composition is an oil-in-water emulsion comprising squalene as an oil component, L-α-phosphatidylcholine and Poloxamer 188.

[15] The pharmaceutical composition according to [13] or [14] where the oil-in-water emulsion comprises droplets with a mean particle size of 10-1000 nm±10 nm.

[16] The pharmaceutical composition according to any one of [12] to [15], further comprising an antigen.

[17] The pharmaceutical composition according to [16], wherein the antigen is an antigen derived from a pathogen or is a tumor antigen.

[18] The pharmaceutical composition according to [16] or [17], wherein the antigen is a peptide or a protein.

[19] A vaccine adjuvant comprising a compound represented by the formula (1) according to any one of [1] to [11] or its pharmaceutically acceptable salt.

[20] A compound represented by the formula (1) according to any one of [1] to [11] or its pharmaceutically acceptable salt for use in therapy.

[21] A compound represented by the formula (1) according to any one of [1] to [11] or its pharmaceutically acceptable salt for use as a vaccine adjuvant.

[22] A compound represented by the formula (1) according to any one of claims [1] to [11] or its pharmaceutically acceptable salt for use in the treatment or prevention of cancer.

[23] A method of enhancing immunostimulating activity of an antigen comprising a step of administering an effective amount of a compound represented by the formula (1) according to any one of [1] to [11] or its pharmaceutically acceptable salt to a mammal in need thereof.

[24] Use of a compound according to any one of [1] to [11] or its pharmaceutically acceptable salt for the manufacture of a vaccine adjuvant.

BRIEF DESCRIPTION OF DRAWINGS

FIG. 1 Induction of amplified antigen-specific T cell responses by the emulsions of Examples 6, 7 and 8.

FIG. 2 Induction of amplified antigen-specific CD8 T cell responses by the emulsions of Examples 6, 7 and 8.

FIG. 3 Induction of high frequencies of antigen-specific multifunctional CD4 T cells by the emulsions of Examples 6, 7 and 8. GM-CSF+ depicted as G+, IFN-γ+ depicted as g+, IL-2+ depicted as 2+, and TNF-a+ depicted as T+, GM-CSF− depicted as G−, IFNγ-depicted as g−, IL-2− depicted as 2−, and TNF-a− depicted as T−.

FIG. 4 Induction of high frequencies of antigen-specific multifunctional CD4 T cells by the emulsions of Examples 6, 7 and 8. GM-CSF+ depicted as G+, IFN-γ+ depicted as g+, IL-2+ depicted as 2+, and TNF-a+ depicted as T+, GM-CSF− depicted as G−, IFNγ− depicted as g−, IL-2− depicted as 2−, and TNF-a− depicted as T−.

FIG. 5 Induction of robust antigen specific IgG and IgG2c titers in mice by the emulsions of Examples 6, 7 and 8.

FIG. 6 Induction of amplified antigen-specific T cell responses by the emulsion of Example 9.

FIG. 7 Induction of amplified antigen-specific CD8 T cell responses by the emulsion of Example 9.

FIG. 8 Induction of high frequencies of antigen-specific multifunctional CD4 T cells by the emulsion of Example 9.

FIG. 9 Induction of high frequencies of antigen-specific multifunctional CD8 T cells by the emulsion of Example 9. GM-CSF+ depicted as G+, IFN-γ+ depicted as g+, IL-2+ depicted as 2+, and TNF-a+ depicted as T+, GM-CSF− depicted as G−, IFN-γ− depicted as g−, IL-2− depicted as 2−, and TNF-a− depicted as T−.

FIG. 10 Induction of robust antigen specific IgG titers in mice by the emulsion of Example 9.

FIG. 11 Induction of robust antigen specific IgG2a titers in mice by the emulsion of Example 9.

FIG. 12 Induction of robust antigen specific cytotoxic responses in mice by the emulsion of Example 9.

DESCRIPTION OF EMBODIMENTS

The present invention includes any optically-active and racemic substances having the physiological activity described below when the above-defined compound of formula (1) has one or more asymmetric carbon atoms and thereby exists as an optically-active form or a racemic form. The preparation of such optically-active compound can be carried out by a standard organic chemistry technique which is well known in said field, for example, synthesis from an optically-active starting material, or resolution of a racemic substance. The physiological activity in the present invention can be evaluated with a standard experimental technique described below.

In one embodiment there is provided a compound represented by the formula (1) or its pharmaceutically acceptable salt which is a single optical isomer being in an enantiomeric excess (% ee) of ≥95%, ≥98% or ≥99%. In one embodiment, the single optical isomer is present in an enantiomeric excess (% ee) of ≥99%.

The compound of the above formula (1) may exist in the form of a non-solvate or a solvate such as hydrate.

The form of the compound of formula (1) is not limited, and may be in an amorphous form or in a specific crystalline form.

The term "halogen atom" as used herein includes fluorine atom, chlorine atom, bromine atom, and iodine atom, or for example fluorine atom and chlorine atom.

The term "alkylene" as used herein includes a straight or branched chain alkylene group having 1 to 6 carbon atoms. Specific alkylene groups include, but are not limited to, methylene, ethylene, n-propylene, and n-butylene.

The term "alkyl" as used herein includes a straight or branched chain alkyl group having 1 to 6 carbon atoms. Specific alkyl groups include, but are not limited to, methyl, ethyl, propyl, isopropyl, butyl, isobutyl, and tert-butyl.

The term "haloalkyl" as used herein denotes a straight or branched chain alkyl group having 1 to 6 carbon atoms which is substituted with the same or different 1 to 5 halogen atoms. Specific haloalkyl groups include, but are not limited to, difluoromethyl, trifluoromethyl, trichloromethyl, difluoroethyl, trifluoroethyl, tetrafluoroethyl, and pentafluoroethyl.

The term "alkoxy" as used herein includes a straight or branched chain alkoxy group having 1 to 6 carbon atoms. Specific alkoxy groups include, but are not limited to, methoxy, ethoxy, propoxy, isopropoxyl, butoxy, isobutoxy, tert-butoxy, pentoxy, and isopentoxy.

The term "haloalkoxy" as used herein denotes a straight or branched chain alkoxy group having 1 to 6 carbon atoms which is substituted with the same or different 1 to 5 halogen atoms. Specific haloalkoxy groups include, but are not limited to, difluoromethoxy, trifluoromethoxy, trichloromethoxy, difluoroethoxy, trifluoroethoxy, tetrafluoroethoxy, and pentafluoroethoxy.

The term "aromatic carbocycle" as used herein includes monocyclic aromatic carbocycles, for example a benzene ring.

The term "aromatic heterocycle" as used herein includes a 5- to 6-membered monocyclic aromatic heterocycle containing 1 to 4 heteroatoms selected from the group consisting of 1 to 4 nitrogen atoms, one oxygen atom, and one sulfur atom in the ring. Specific aromatic heterocycles include, but are not limited to, a pyrrole ring, a thiophene ring, a furan ring, a pyridine ring, and a pyrimidine ring.

Variable groups in formula (1) may have the following values. Such values may be used in combination with any of the definitions, claims (for example claim 1), or embodiments described herein to provide further embodiments of the invention.

In some embodiments, $L^1$ in formula (1) is $C_{1-4}$ alkylene. In some embodiments, $L^1$ in formula (1) is $C_{1-3}$ alkylene. In some embodiments, $L^1$ in formula (1) is methylene or ethylene. In some embodiments, $L^1$ in formula (1) is methylene.

In some embodiments, $L^2$ in formula (1) is $C_{1-4}$ alkylene. In some embodiments, $L^2$ in formula (1) is methylene or ethylene. In some embodiments, $L^2$ in formula (1) is methylene.

In some embodiments, $X^1$ in formula (1) is a single bond, oxygen atom, sulfur atom, sulfinyl group, sulfonyl group, $NR^4$ or $CONR^4$ wherein $R^4$ is hydrogen atom or $C_{1-4}$ alkyl group. In some embodiments, $X^1$ in formula (1) is a single bond, oxygen atom, $NR^4$ or $CONR^4$. In some embodiments, $X^1$ in formula (1) is oxygen atom.

In some embodiments, $R^4$ in formula (1) is hydrogen atom or $C_{1-3}$ alkyl group. In some embodiments, $R^4$ in formula (1) is hydrogen atom or methyl group.

In some embodiments, m in formula (1) is 1. In some embodiments, m in formula (1) is 0.

In some embodiments, the bonds described by
[Chem.7]

are independently a single bond or a double bond. In some embodiments, the bonds described by
[Chem.8]

are all single bonds or all double bonds. In some embodiments, the bonds described by
[Chem.9]

are all single bonds.

In some embodiments, $R^1$ in formula (1) is hydrogen atom or $C_{1-3}$ alkyl group. In some embodiments, $R^1$ in formula (1) is hydrogen atom or methyl group. In some embodiments, $R^1$ in formula (1) is methyl.

In some embodiments, $R^2$ in formula (1) is a substituted or unsubstituted alkyl group having 1 to 6 carbon atoms. In some embodiments, $R^2$ in formula (1) is a substituted or unsubstituted alkyl group having 1 to 4 carbon atoms.

In any embodiment where an alkyl group is substituted, said alkyl may be substituted with the same or different 1 to 4 substituents selected from the following group: hydroxy group, halogen atom, $C_{1-6}$ alkyl group, $C_{1-6}$ haloalkyl group, $C_{1-6}$ alkoxy group, $C_{1-6}$ haloalkoxy group, amino group which may be substituted with one or two $C_{1-6}$ alkyl group, and carboxy group.

In any embodiment where an alkyl group is substituted, said alkyl may be substituted with the same or different 1 to 3 substituents selected from hydroxy group, halogen atom, $C_{1-6}$ alkoxy group, and $C_{1-6}$ haloalkoxy group, and more preferably hydroxy group or $C_{1-4}$ alkoxy group.

In some embodiments, $R^2$ in formula (1) is $C_{1-6}$ alkyl group, $C_{2-4}$ alkyl group substituted with $C_{1-3}$ alkoxy group, or $C_{2-6}$ alkyl group substituted with 1 to 4 hydroxyl groups provided that the hydroxyl groups are attached to different carbon atoms when the $C_{2-6}$ alkyl group is substituted with plural hydroxyl groups. In some embodiments, $R^2$ in formula (1) is $C_{1-6}$ alkyl group. In some embodiments, $R^2$ in formula (1) is $C_{2-4}$ alkyl group substituted with $C_{1-3}$ alkoxy group. In some embodiments, $R^2$ in formula (1) is $C_{2-6}$ alkyl group substituted with 1 to 4 hydroxyl groups provided that the hydroxyl groups are attached to different carbon atoms when the $C_{2-6}$ alkyl group is substituted with plural hydroxyl groups. In some embodiments, $R^2$ in formula (1) is n-butyl, 2-methoxyethyl, or 2,3-dihydroxyprop-1-yl. In some embodiments, $R^2$ in formula (1) is n-butyl. In some embodiments, $R^2$ in formula (1) is 2-methoxyethyl. In some embodiments, $R^2$ in formula (1) is 2,3-dihydroxyprop-1-yl.

In some embodiments, "A" in formula (1) is benzene ring or a monocyclic aromatic heterocycle containing 1 to 4 heteroatoms selected from the group consisting of 1 to 4 nitrogen atoms, one oxygen atom and one sulfur atom in the ring. In some embodiments, "A" in formula (1) is benzene ring, pyridine ring, pyrrole ring, thiophene, furan ring, or pyrimidine ring. In some embodiments, "A" in formula (1) is benzene ring or pyridine ring. In some embodiments, "A" in formula (1) is benzene ring.

In some embodiments, $R^3$ in formula (1) is hydrogen atom, halogen atom, $C_{1-6}$ alkyl group or $C_{1-6}$ alkoxy group. In some embodiments, $R^3$ in formula (1) is hydrogen atom, fluorine atom, chlorine atom, $C_{1-3}$ alkyl group, or $C_{1-3}$ alkoxy group. In some embodiments, $R^3$ in formula (1) is hydrogen atom, fluorine atom, methyl group or methoxy group. In some embodiments, $R^3$ in formula (1) is hydrogen atom.

In one embodiment, there is provided a compound represented by the formula (1) or its pharmaceutically acceptable salt wherein $L^1$ and $L^2$ are methylene, $R^1$ is hydrogen atom or methyl group, $R^2$ is $C_{1-6}$ alkyl group, $C_{2-4}$ alkyl group substituted with $C_{1-3}$ alkoxy group, or $C_{2-6}$ alkyl group substituted with 1 to 4 hydroxyl groups provided that the hydroxyl groups are attached to different carbon atoms when the $C_{2-6}$ alkyl group is substituted with plural hydroxyl groups, $R^3$ is hydrogen atom, $C_{1-3}$ alkyl group, $C_{1-3}$ alkoxy group or halogen atom, $X^1$ is a single bond, oxygen atom, or $NR^4$ wherein $R^4$ is hydrogen atom or $C_{1-3}$ alkyl group, A is benzene ring or pyridine ring, and all of the bonds described by
[Chem.10]

represent a single bond, or all of the bonds described by
[Chem.11]

represent a double bond.

In one embodiment, there is provided a compound represented by the formula (1) or its pharmaceutically acceptable salt wherein
$L^1$ and $L^2$ are methylene,
$R^1$ is hydrogen atom or methyl group,
$R^2$ is $C_{1-6}$ alkyl group, $C_{2-4}$ alkyl group substituted with $C_{1-3}$ alkoxy group, or $C_{2-6}$ alkyl group substituted with 1 to 4 hydroxyl groups provided that the hydroxyl groups are attached to different carbon atoms when the $C_{2-6}$ alkyl group is substituted with plural hydroxyl groups,
$R^3$ is hydrogen atom, $C_{1-3}$ alkyl group, $C_{1-3}$ alkoxy group or halogen atom,
$X^1$ is a single bond, oxygen atom, or $NR^4$ wherein $R^4$ is hydrogen atom or $C_{1-3}$ alkyl group,
A is benzene ring or pyridine ring, and
all of the bonds described by
[Chem.12] ═══
represent a single bond, or all of the bonds described by
[Chem.13]
═══
represent a double bond.

In one embodiment, there is provided a compound represented by the formula (1) or its pharmaceutically acceptable salt wherein
$L^1$ and $L^2$ are methylene,
$R^1$ is methyl group,
$R^2$ is $C_{1-6}$ alkyl group, $C_{2-4}$ alkyl group substituted with $C_{1-3}$ alkoxy group, or $C_{2-6}$ alkyl group substituted with 1 to 4 hydroxyl groups provided that the hydroxyl groups are attached to different carbon atoms when the $C_{2-6}$ alkyl group is substituted with plural hydroxyl groups,
$R^3$ is hydrogen atom,
$X^1$ is oxygen atom,
A is benzene ring, and
all of the bonds described by
[Chem.14]
═══
represent a single bond.

In one embodiment, there is provided a compound represented by the formula (1) or its pharmaceutically acceptable salt wherein
$L^1$ and $L^2$ are methylene,
$R^1$ is methyl group,
$R^2$ is n-butyl, 2-methoxyethyl, or 2,3-dihydroxyprop-1-yl,
$R^3$ is hydrogen atom,
$X^1$ is oxygen atom,
A is benzene ring, and
all of the bonds described by
[Chem.15]
═══
represent a single bond.

In one embodiment there is provided a compound represented by the formula (1) which is 6 amino-2-butoxy-9-[4-({[(4E,8E,12E,16E,20E)-4,8,12,17,21,25-hexamethylhexacosa-4,8,12,16,20,24-hexaen-1-yl](methyl)amino}methyl)benzyl]-7,9-dihydro-8H-purin-8-one or its pharmaceutically acceptable salt. In one embodiment there is provided a compound represented by the formula (1) which is 6-amino-2-butoxy-9-[4-({[(4E,8E,12E,16E,20E)-4,8,12,17,21,25-hexamethylhexacosa-4,8,12,16,20,24-hexaen-1-yl](methyl)amino}methyl)benzyl]-7,9-dihydro-8H-purin-8-one. In one embodiment there is provided a compound represented by the formula (1) which is a pharmaceutically acceptable salt of 6-amino-2-butoxy-9-[4-({[(4E,8E,12E,16E,20E)-4,8,12,17,21,25-hexamethylhexacosa-4,8,12,16,20,24-hexaen-1-yl](methyl)amino}methyl)benzyl]-7,9-dihydro-8H-purin-8-one.

In one embodiment there is provided a compound represented by the formula (1) which is 6 amino-9-[4-({[(4E,8E,12E,16E,20E)-4,8,12,17,21,25-hexamethylhexacosa-4,8,12,16,20,24-hexaen-1-yl](methyl)amino}methyl)benzyl]-2-(2-methoxyethoxy)-7,9-dihydro-8H-purin-8-one or its pharmaceutically acceptable salt. In one embodiment there is provided a compound represented by the formula (1) which is 6-amino-9-[4-({[(4E,8E,12E,16E,20E)-4,8,12,17,21,25-hexamethylhexacosa-4,8,12,16,20,24-hexaen-1-yl](methyl)amino}methyl)benzyl]-2-(2-methoxyethoxy)-7,9-dihydro-8H-purin-8-one. In one embodiment there is provided a compound represented by the formula (1) which is a pharmaceutically acceptable salt of 6-amino-9-[4-({[(4E,8E,12E,16E,20E)-4,8,12,17,21,25-hexamethylhexacosa-4,8,12,16,20,24-hexaen-1-yl](methyl)amino}methyl)benzyl]-2-(2-methoxyethoxy)-7,9-dihydro-8H-purin-8-one.

In one embodiment there is provided a compound represented by the formula (1) which is 3-({6-amino-9-[4-({[(4E,8E,12E,16E,20E)-4,8,12,17,21,25-hexamethylhexacosa-4,8,12,16,20,24-hexaen-1-yl](methyl)amino}methyl)benzyl]-8-hydroxy-9H-purin-2-yl}-oxy)propane-1,2-diol or its pharmaceutically acceptable salt. In one embodiment there is provided a compound represented by the formula (1) which is 3-({6-amino-9-[4-({[(4E,8E,12E,16E,20E)-4,8,12,17,21,25-hexamethylhexacosa-4,8,12,16,20,24-hexaen-1-yl](methyl)amino}methyl)benzyl]-8-hydroxy-9H-purin-2-yl}-oxy)propane-1,2-diol. In one embodiment there is provided a compound represented by the formula (1) which is a pharmaceutically acceptable salt of 3-({6-amino-9-[4-({[(4E,8E,12E,16E,20E)-4,8,12,17,21,25-hexamethylhexacosa-4,8,12,16,20,24-hexaen-1-yl](methyl)amino}methyl)benzyl]-8-hydroxy-9H-purin-2-yl}-oxy)propane-1,2-diol.

The pharmaceutically acceptable salt of the compound of formula (1) includes, for example, acid addition salts or base addition salts. The acid addition salts include a salt with an inorganic or organic acid such as hydrochloride, hydrobromide, sulfate, trifluoroacetate, citrate and maleate. The base addition salts include an alkaline metal salt such as sodium salt and potassium salt, an alkaline earth metal salt such as calcium salt, and an ammonium salt.

In one embodiment there is provided a compound represented by the formula (1) or its pharmaceutically acceptable salt where the pharmaceutically acceptable salt is a hydrochloride, hydrobromide, sulfate, trifluoroacetate, citrate, maleate, sodium salt, potassium salt, calcium salt or ammonium salt. In one embodiment there is provided a compound represented by the formula (1) or its pharmaceutically acceptable salt where the pharmaceutically acceptable salt is a hydrochloride, hydrobromide, sulfate, trifluoroacetate, citrate or maleate salt. In one embodiment there is provided a compound represented by the formula (1) or its pharmaceutically acceptable salt where the pharmaceutically acceptable salt is a sodium, potassium, calcium or ammonium salt.

Process to Prepare the Compound of Formula (1)

The compounds of formula (1) can be prepared using known compounds as a starting material according to the following processes.

The starting materials may be used in the form of a salt. The following processes are only examples, and the present compounds can be also prepared by other processes based on a skilled person's knowledge.

Process 1

For example, the compound of formula (1) or its pharmaceutically acceptable salt can be prepared according to the following process.

[Chem. 16]

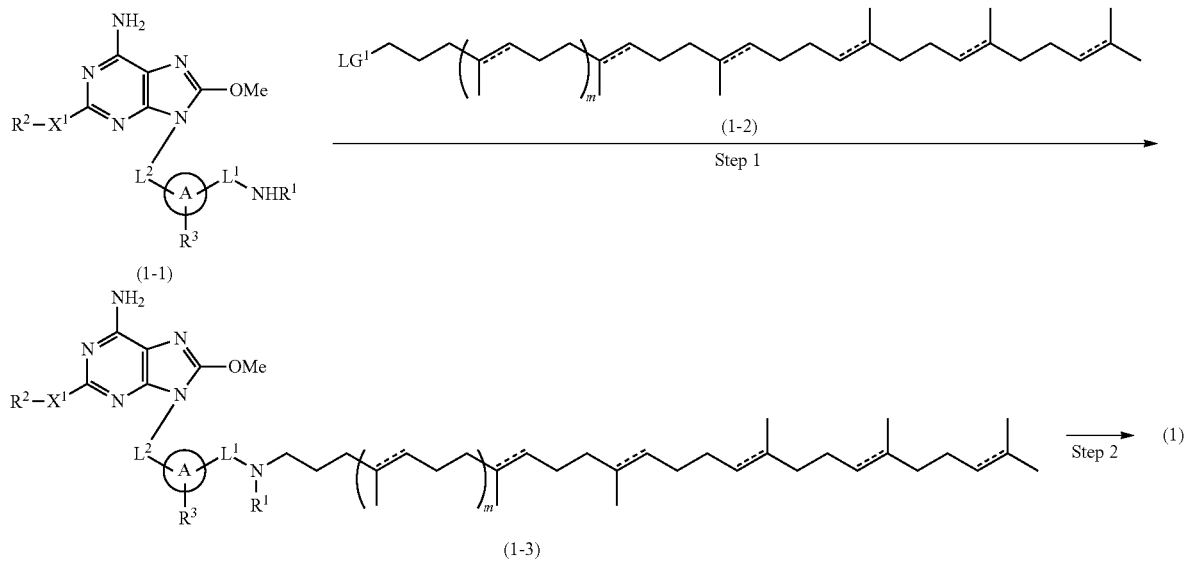

Wherein A, $L^1$, $L^2$, $X^1$, $R^1$, $R^2$, $R^3$, and m are as defined above, and $LG^1$ means a leaving group.

Step 1

Compounds of formula (1-1) can be prepared according to WO 2008/114817. Specifically, they can be prepared by reacting Compounds of formula (1-5) [prepared from 2,6-dichloro-9-(tetrahydro-2H-pyran-2-yl)-9H-purine (formula (1-4)] with Compounds of formula (1-6) in the presence of a base.

[Chem. 17]

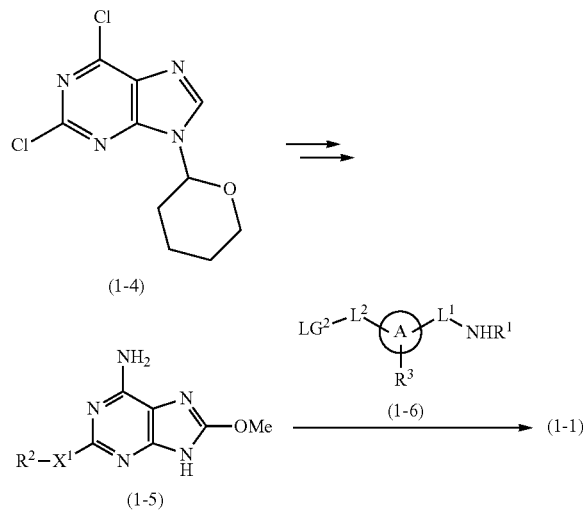

In the above scheme, A, $L^1$, $L^2$, $X^1$, $R^1$, $R^2$ and $R^3$ are as defined above, and $LG^2$ is a leaving group. Compounds of formula (1-3) can be prepared by reacting Compounds of formula (1-1) with Compounds of formula (1-2) in an inert solvent in the presence of a base.

The base used herein includes, an organic base or an inorganic base which are available to the skilled person in the art, for example, an organic base such as N-methylmorpholine, triethylamine, diisopropylethylamine, tributylamine, 1,8-diazabicyclo[4.3.0]non-5-ene, 1,4-diazabicyclo[5.4.0]undec-7-ene, pyridine, or dimethylaminopyridine; and an inorganic base such as sodium hydrogen carbonate, potassium hydrogen carbonate, sodium carbonate, potassium carbonate, cesium carbonate, sodium hydroxide, or sodium hydride. The amount of the base used herein is generally 0.1 to 100 moles, or alternatively 1 to 3 moles, per 1 mole of Compound (1-1).

The inert solvent used herein includes, for example, an ether solvent such as tetrahydrofuran, diethyl ether, 1,4-dioxane, or 1,2-dimethoxyethane; a hydrocarbon solvent such as hexane, heptane, toluene, benzene, or xylene; and a non-proton solvent such as acetonitrile, N,N'-dimethyl formamide, N-methylpyrrolidone, or dimethylsulfoxide; or any suitable mixture thereof. The reaction temperature is for example in the range of about 0° C. to about 120° C.

The leaving group $LG^1$ in Compounds of formula (1-2) in Step 1 includes, but is not limited to, a halogen atom or alkyl sulfonyloxy group, or aryl sulfonyloxy group. For example, Compounds of formula (1-2) can be prepared according to the reference (Org. Biomol. Chem. 2011, 9, 4367) when $LG^1$ is a methanesulfonyloxy group. When $LG^1$ is a halogen or other leaving groups, Compounds of formula (1-2) can be also prepared from an intermediate described in the reference under conventional conditions that a skilled person well knows (Journal of the Chemical Society, Perkin Transaction 11, Organic and Bio-Organic Chemistry, (7), 889-93 (1995)). For example, the Compounds of formula (1-2) wherein $LG^1$ is bromine (Formula (1-7)) can be synthesized from a hydroxy compound of Formula (1-6) with carbon tetrabromide and triphenylphosphine in dichloromethane or ether solvent, as shown in the following scheme.

[Chem.18]

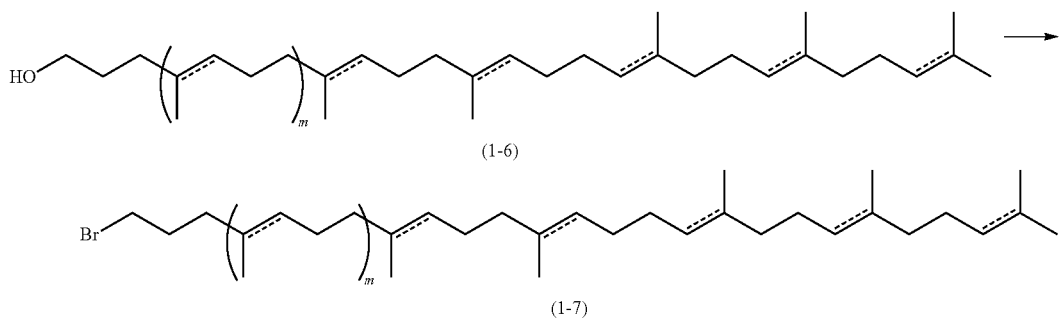

The leaving group LG² in Compounds of formula (1-6) is, for example, halogen, alkylsulphonyl or optionally substituted arylsulphonyl group.

Step 2

Compounds of formula (1) can be prepared by reacting Compounds of formula (1-3) under acidic conditions. The acid used may be for example hydrochloric acid or trifluoroacetic acid. The amount of the acid used may be for example 0.1 molar equivalents to an excess of 20 moles per 1 mole of Compound of formula (1-3). The hydrochloric acid can be used as an aqueous solution, or as a solution in an organic solvent such as methanol or 1,4-dioxane. The solvent used in Step 2 includes, for example, an ether solvent such as tetrahydrofuran, diethyl ether, 1,4-dioxane, or 1,2-dimethoxyethane; a halogen solvent such as dichloromethane, chloroform, or 1,2-dichloroethane; and an alcohol solvent such as methanol, ethanol, or isopropanol; or a mixture thereof. The reaction temperature is preferably selected from, but not limited to, the range of about 0° C. to about 60° C.

Process 2

Compounds of formula (1-3) or their salts can also be prepared according to the following process.

Wherein A, L¹, L², X¹, R¹, R², R³, and m are as defined above, and LG³ means a leaving group.

Step 1

Compounds of formula (2-1) can be prepared according to WO 2008/114817. The leaving group LG³ in Compounds of formula (2-2) includes, but is not limited to, halogen atom, alkyl sulfonyloxy group, and aryl sulfonyloxy group. Compounds of formula (2-2) can be prepared, for example, by reacting Compounds of formula (2-1) with methanesulfonyl chloride, p-toluenesulfonyl chloride or the like in the presence of a base such as triethylamine, diisopropylethylamine, pyridine, dimethylaminopyridine, sodium carbonate, or potassium carbonate.

Step 2

Compounds of formula (1-3) can be prepared from Compounds of formula (2-2) and Compounds of formula (2-3) using the same conditions used in Step 1 in Process 1.

Compounds of formula (2-3) wherein m is 0 can be prepared according to a synthetic method well-known by a skilled person (e.g. J. Am. Chem. Soc. 1989, 111, 1508; Lipids, 2005, 40, 729; J. Org. Chem. 1996, 61, 3849), including reductive amination of 1,1',2-tris-nor-squalene aldehyde. Compounds of formula (2-3) wherein m is 1 can

[Chem. 19]

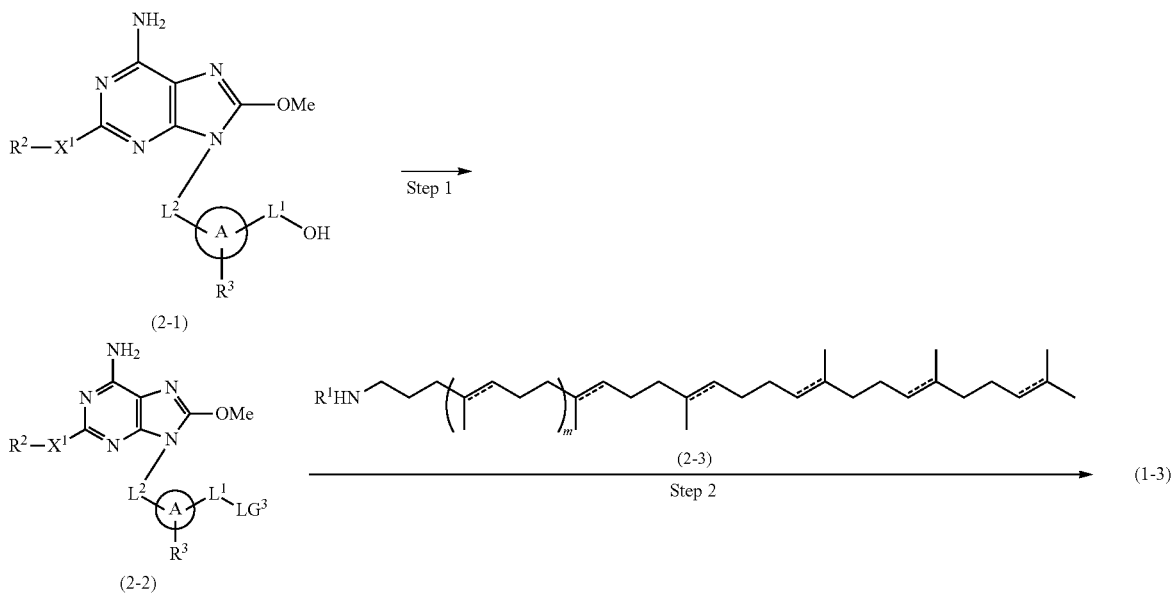

be prepared according to a method well-known by a skilled person (e.g. Org. Biomol. Chem. 2011, 9, 4367).

In addition, Compounds of formula (2-3) wherein $R^1$ is an alkyl group (i.e., Compounds of formula (2-5) in the scheme shown below) can be prepared, for example, by the process shown in the following scheme.

[Chem.20]

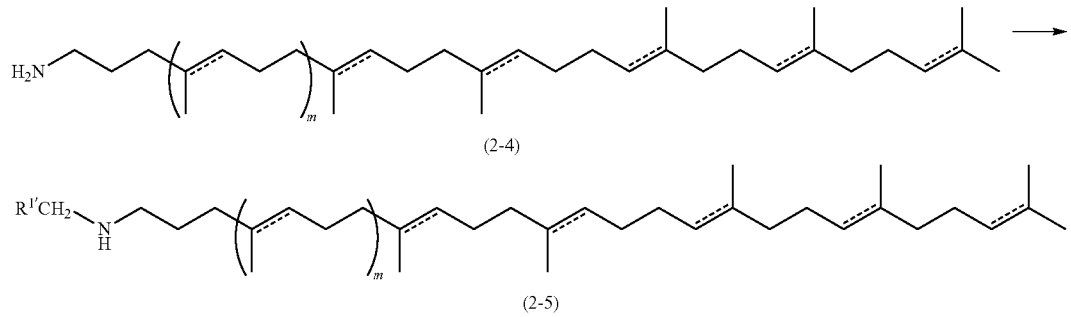

Wherein m is as defined above, and $R^{1'}CH_2$ corresponds to $R^1$ as defined above.

Compounds of formula (2-5) can be prepared from Compounds of formula (2-4) and an aldehyde compound ($R^{1'}CHO$) under reductive amination conditions well-known by a skilled person.

In addition, Compounds of formula (2-3) can be prepared according to the following scheme, i.e., where a Compound of formula (2-4) is converted to a Compound of formula (2-6) by protecting the amino group therein, the resulting Compound of formula (2-6) then being alkylated under conditions well-known by a skilled person to provide a Compound of formula (2-7), and then the resulting Compound of formula (2-7) being deprotected to prepare a Compound of formula (2-3).

Wherein $R^1$ is defined as above, and PG means a protective group suitable for protecting an amino group.

The protective group PG may be any protective group well-known by a skilled person such as acetyl, trifluoroacetyl, Boc, or Fmoc, and the step of protection and deprotection can be done according to the conditions known to the skilled person, or as described in a suitable textbook reference (e.g. Protective Groups in Organic Synthesis 3rd Edition (John Wiley & Sons, Inc. 2002)).

Process 3

Compounds of formula (1-3) or their salts can be also prepared according to the following process.

[Chem.21]

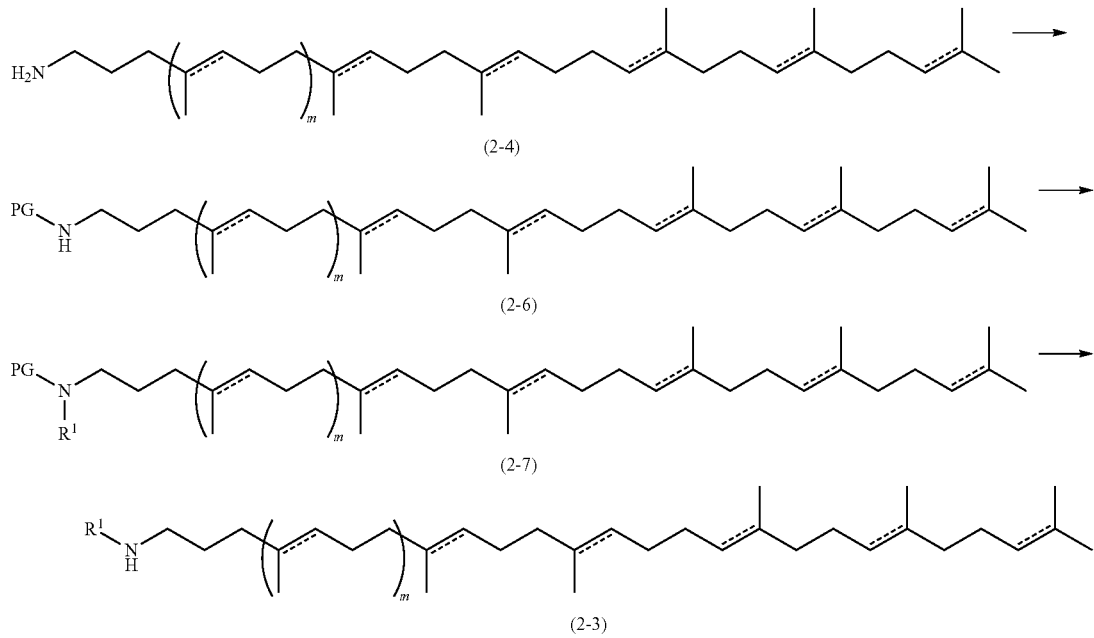

[Chem. 22]

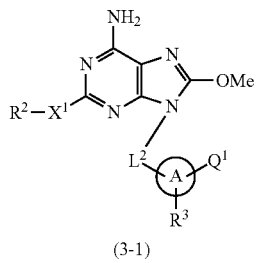

(3-1)

(3-1)
Wherein A, $L^1$, $L^2$, $X^1$, $R^1$, $R^2$, $R^3$, and m are as defined above, and (1) $Q^1$ is -$L^1$$NHR^1$ and $Q^2$ is CHO, or (2) $Q^1$ is -$L^{1'}$-CHO wherein $L^{1'}$ is absent or an alkylene and -$L^{1'}$-$CH_2$— corresponds to -$L^1$-, and $Q^2$ is —$CH_2NHR^1$.

Compounds of formula (1-3) can be prepared by condensing Compounds of formula (3-1) and Compounds of formula (3-2) under reductive amination conditions well-known by a skilled person.

Compounds of formula (3-1) can be prepared according to a conventional process (e.g. as described in WO 2008/114817). In addition, Compounds of formula (3-1) wherein $Q^1$ is -$L^{1'}$-CHO can be prepared by oxidizing Compounds of formula (2-1) prepared in Process 2 with an oxidation agent such as manganese dioxide.

In any of the preparative steps described herein, if it is necessary to protect a specific functional group therein (such as hydroxyl group and amino group), the functional group can be protected with one or more suitable protective groups and then deprotected in a suitable manner according to a method well-known by a skilled person, for examples as described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The intermediates described above are useful in the preparation of compounds of formula (1) and therefore form a further embodiment.

In one embodiment, there is provided a compound represented by the formula (1-3) or its salt:

$X^1$ is single bond, oxygen atom, sulfur atom, SO, $SO_2$, $NR^4$ or $CONR^4$;

$R^4$ is hydrogen atom or alkyl;

A is monocyclic aromatic carbocycle, or 5- or 6-membered aromatic heterocycle which includes 1 to 4 heteroatoms selected from the group consisting of 1 to 4 nitrogen atoms, an oxygen atom and a sulfur atom;

m is 0 or 1; and a bond described by
[Chem.24]
===== independently represents a single bond or a double bond.

In one embodiment, there is provided a compound of formula (1-3) or a salt thereof, wherein $L^1$ and $L^2$ are methylene, $R^1$ is hydrogen atom or methyl group, $R^2$ is $C_{1-6}$ alkyl group, $C_{2-4}$ alkyl group substituted with $C_{1-3}$ alkoxy group, or $C_{2-6}$ alkyl group substituted with 1 to 4 hydroxyl groups provided that the hydroxyl groups are attached to different carbon atoms when the $C_{2-6}$ alkyl group is substituted with plural hydroxyl groups, $R^3$ is hydrogen atom, $C_{1-3}$ alkyl group, $C_{1-3}$ alkoxy group or halogen atom, $X^1$ is single bond, oxygen atom, or $NR^4$ wherein $R^4$ is hydrogen atom or $C_{1-3}$ alkyl group, A is benzene ring or pyridine ring, and all of the bonds described by
[Chem.25]
===== represent a single bond, or all of the bonds described by
[Chem.26]
==== represent a double bond.

[Chem.23]

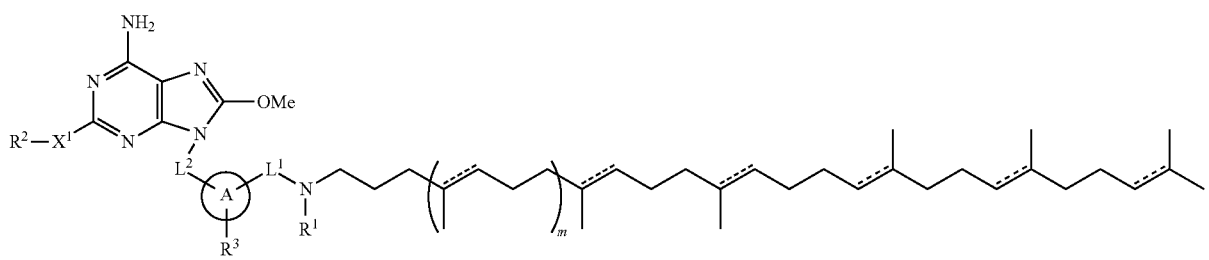

(1-3)

wherein $L^1$ and $L^2$ are independently alkylene;

$R^1$ is hydrogen atom or alkyl;

$R^2$ is optionally substituted alkyl;

$R^3$ is hydrogen atom, halogen atom, alkyl or alkoxy;

In one embodiment, there is provided a compound represented by the formula (1-3) or its salt wherein $L^1$ and $L^2$ are methylene, $R^1$ is hydrogen atom or methyl group, $R^2$ is $C_{1-6}$ alkyl group, $C_{2-4}$ alkyl group substituted with $C_{1-3}$ alkoxy group, or $C_{2-6}$ alkyl group substituted with 1 to 4 hydroxyl groups provided that the hydroxyl groups are attached to different carbon atoms when the $C_{2-6}$ alkyl group is substituted with plural hydroxyl groups, $R^3$ is hydrogen atom, $C_{1-3}$ alkyl group, $C_{1-3}$ alkoxy group or halogen atom, $X^1$ is single bond, oxygen atom, or $NR^4$ wherein $R^4$ is hydrogen atom or $C_{1-3}$ alkyl group, A is benzene ring or pyridine ring, and all of the bonds described by

[Chem.27]

===== represent a single bond, or all of the bonds described by

[Chem.28]

===== represent a double bond.

In one embodiment, there is provided a compound represented by the formula (1-3) or its salt wherein $L^1$ and $L^2$ are methylene, $R^1$ is hydrogen atom or methyl group, $R^2$ is $C_{1-6}$ alkyl group, $C_{2-4}$ alkyl group substituted with $C_{1-3}$ alkoxy group, or $C_{2-6}$ alkyl group substituted with 1 to 4 hydroxyl groups provided that the hydroxyl groups are attached to different carbon atoms when the $C_{2-6}$ alkyl group is substituted with plural hydroxyl groups, $R^3$ is hydrogen atom, $C_{1-3}$ alkyl group, $C_{1-3}$ alkoxy group or halogen atom, $X^1$ is a single bond, oxygen atom, or $NR^4$ wherein $R^4$ is hydrogen atom or $C_{1-3}$ alkyl group, A is benzene ring or pyridine ring, and all of the bonds described by

[Chem.29]

===== represent a single bonds, or all of the bonds described by

[Chem.30]

===== represent a double bond.

In one embodiment, there is provided a compound represented by the formula (1-3) or its salt wherein $L^1$ and $L^2$ are methylene, $R^1$ is hydrogen atom or methyl group, $R^2$ is $C_{1-6}$ alkyl group, $C_{2-4}$ alkyl group substituted with $C_{1-3}$ alkoxy group, or $C_{2-6}$ alkyl group substituted with 1 to 4 hydroxyl groups provided that the hydroxyl groups are attached to different carbon atoms when the $C_{2-6}$ alkyl group is substituted with plural hydroxyl groups, $R^3$ is hydrogen atom, $C_{1-3}$ alkyl group, $C_{1-3}$ alkoxy group or halogen atom, $X^1$ is a single bond, oxygen atom, or $NR^4$ wherein $R^4$ is hydrogen atom or $C_{1-3}$ alkyl group, A is benzene ring or pyridine ring, and all of the bonds described by

[Chem.31]

===== represent a single bond, or all of the bonds described by

[Chem.32] ===== represent a double bond.

In one embodiment, there is provided a compound represented by the formula (1-3) or its salt wherein $L^1$ and $L^2$ are methylene, $R^1$ is methyl group, $R^2$ is $C_{1-6}$ alkyl group, $C_{2-4}$ alkyl group substituted with $C_{1-3}$ alkoxy group, or $C_{2-6}$ alkyl group substituted with 1 to 4 hydroxyl groups provided that the hydroxyl groups are attached to different carbon atoms when the $C_{2-6}$ alkyl group is substituted with plural hydroxyl groups, $R^3$ is hydrogen atom, $X^1$ is oxygen atom, A is benzene ring, and all of the bonds described by

[Chem.33]

===== represent a single bond.

In one embodiment, there is provided a compound represented by the formula (1-3) or its salt wherein $L^1$ and $L^2$ are methylene, $R^1$ is methyl group, $R^2$ is n-butyl, 2-methoxyethyl, or 2,3-dihydroxyprop-1-yl, $R^3$ is hydrogen atom, $X^1$ is oxygen atom, A is benzene ring, and all of the bonds described by

[Chem.34] ===== represent a single bond.

In one embodiment there is provided 2-butoxy-9-[[4-[[[(4E,8E,12E,16E,20E)-4,8,12,17,21,25-hexamethylhexacosa-4,8,12,16,20,24-hexaenyl]-methyl-amino]methyl]phenyl]methyl]-8-methoxy-purin-6-amine, or a salt thereof. In one embodiment there is provided 2-butoxy-9-[[4-[[[(4E,8E,12E,16E,20E)-4,8,12,17,21,25-hexamethylhexacosa-4,8,12,16,20,24-hexaenyl]-methyl-amino]methyl]phenyl]methyl]-8-methoxy-purin-6-amine. In one embodiment there is provided a salt of 2-butoxy-9-[[4-[[[(4E,8E,12E,16E,20E)-4,8,12,17,21,25-hexamethylhexacosa-4,8,12,16,20,24-hexaenyl]-methyl-amino]methyl]phenyl]methyl]-8-methoxy-purin-6-amine.

In one embodiment there is provided 9-[[4-[[[(4E,8E,12E,16E,20E)-4,8,12,17,21,25-hexamethylhexacosa-4,8,12,16,20,24-hexaenyl]-methyl-amino]methyl]phenyl]methyl]-8-methoxy-2-(2-methoxyethoxy)purin-6-amine, or a salt thereof. In one embodiment there is provided 9-[[4-[[[(4E,8E,12E,16E,20E)-4,8,12,17,21,25-hexamethylhexacosa-4,8,12,16,20,24-hexaenyl]-methyl-amino]methyl]phenyl]methyl]-8-methoxy-2-(2-methoxyethoxy)purin-6-amine. In one embodiment there is provided a salt of 9-[[4-[[[(4E,8E,12E,16E,20E)-4,8,12,17,21,25-hexamethylhexacosa-4,8,12,16,20,24-hexaenyl]-methyl-amino]methyl]phenyl]methyl]-8-methoxy-2-(2-methoxyethoxy)purin-6-amine.

In one embodiment there is provided (2-[(2,2-dimethyl-1,3-dioxolan-4-yl)methoxy]-9-[[4-[[[(4E,8E,12E,16E,20E)-4,8,12,17,21,25-hexamethylhexacosa-4,8,12,16,20,24-hexaenyl]-methyl-amino]methyl]phenyl]methyl]-8-methoxy-purin-6-amine), or a salt thereof. In one embodiment there is provided (2-[(2,2-dimethyl-1,3-dioxolan-4-yl)methoxy]-9-[[4-[[[(4E,8E,12E,16E,20E)-4,8,12,17,21,25-hexamethylhexacosa-4,8,12,16,20,24-hexaenyl]-methyl-amino]methyl]phenyl]methyl]-8-methoxy-purin-6-amine). In one embodiment there is provided a salt of (2-[(2,2-dimethyl-1,3-dioxolan-4-yl)methoxy]-9-[[4-[[[(4E,8E,12E,16E,20E)-4,8,12,17,21,25-hexamethylhexacosa-4,8,12,16,20,24-hexaenyl]-methyl-amino]methyl]phenyl]methyl]-8-methoxy-purin-6-amine).

In any of the embodiments where a compound of formula (1-3) or its salt is mentioned, it is to be understood that such salts do not need to be pharmaceutically acceptable salts. The salt of the compound of formula (1-3) includes, for example, acid addition salts or base addition salts. The acid addition salts include a salt with an inorganic or organic acid such as hydrochloride, hydrobromide, sulfate, trifluoroacetate, citrate and maleate. The base addition salts include an alkaline metal salt such as sodium salt and potassium salt, an alkaline earth metal salt such as calcium salt, and an ammonium salt.

In one embodiment there is provided a compound represented by the formula (1-3) or its salt, where the salt is a hydrochloride, hydrobromide, sulfate, trifluoroacetate, citrate, maleate, sodium salt, potassium salt, calcium salt or ammonium salt. In one embodiment there is provided a compound represented by the formula (1-3) or its salt, where the salt is a hydrochloride, hydrobromide, sulfate, trifluoroacetate, citrate or maleate salt. In one embodiment there is provided a compound represented by the formula (1-3) or its salt, where the salt is a sodium, potassium, calcium or ammonium salt.

Compounds represented by the formula (1) or their pharmaceutically acceptable salts may be administered as a pharmaceutical composition comprising the compounds or salts in combination or association with one or more pharmaceutically acceptable diluents or carriers.

The formulation of the pharmaceutical composition includes injectable liquids, which may comprise emulsions prepared by mixing an aqueous solution and an oily composition, which injectable liquids may be optionally sterilized.

The aqueous solution includes an aqueous solution comprising distilled water for injection, and optional buffer (pH regulator), stabilizing agent, and isotonic agent. Suitable oily compositions include squalene, and squalane.

The compositions of the present invention may further comprise other additives which include, for example, surfactants, pH regulators, and anti-oxidants.

Therefore, in one embodiment there is provided a pharmaceutical composition comprising a compound represented by the formula (1) or its pharmaceutically acceptable salt.

In one embodiment there is provided a pharmaceutical composition comprising a compound represented by the formula (1) or its pharmaceutically acceptable salt in combination with a pharmaceutically acceptable diluent or carrier.

In one embodiment there is provided a pharmaceutical composition comprising a compound represented by the formula (1) or its pharmaceutically acceptable salt, where the pharmaceutical composition is an oil-in-water emulsion.

In one embodiment there is provided a pharmaceutical composition comprising a compound represented by the formula (1) or its pharmaceutically acceptable salt where the pharmaceutical composition is an oil-in-water emulsion comprising squalene as an oil component. In one embodiment, the oil-in-water emulsion comprises 0.1-10% w/w squalene. In one embodiment, the oil-in-water emulsion comprises 1-5% w/w squalene. In one embodiment, the oil-in-water emulsion comprises 2-3% w/w squalene. In one embodiment, the oil-in-water emulsion comprises 2.5%±0.1% w/w squalene. In one embodiment, the oil-in-water emulsion comprises 2.5% w/w squalene.

In one embodiment there is provided a pharmaceutical composition comprising a compound represented by the formula (1) or its pharmaceutically acceptable salt where the pharmaceutical composition is an oil-in-water emulsion further comprising at least one surfactant. In one embodiment, the pharmaceutical composition comprises one or more surfactants that may be the same or different selected from Span (Registered Trademark) 85 (Sorbitan Trioleate), Poloxamer 188 and L-α-phosphatidylcholine. In one embodiment, the surfactant comprises one or more surfactants that may be the same or different selected from 0.01-5% w/w Span (Registered Trademark) 85 (Sorbitan Trioleate) and 0.01-5% w/w Poloxamer 188.

In one embodiment the L-α-phosphatidylcholine is derived from egg.

In one embodiment there is provided a pharmaceutical composition comprising a compound represented by the formula (1) or its pharmaceutically acceptable salt where the pharmaceutical composition is an oil-in-water emulsion comprising squalene as an oil component, Span (Registered Trademark) 85 (Sorbitan Trioleate) and Poloxamer 188.

In one embodiment there is provided a pharmaceutical composition comprising a compound represented by the formula (1) or its pharmaceutically acceptable salt where the pharmaceutical composition is an oil-in-water emulsion comprising 0.1-10% w/w squalene as an oil component, 0.01-5% w/w Span (Registered Trademark) 85 (Sorbitan Trioleate) and 0.01-5% w/w Poloxamer 188.

In one embodiment there is provided a pharmaceutical composition comprising a compound represented by the formula (1) or its pharmaceutically acceptable salt where the pharmaceutical composition is an oil-in-water emulsion comprising 2.5% w/w squalene as an oil component, 0.23% w/w Span (Registered Trademark) 85 (Sorbitan Trioleate) and 0.3% w/w Poloxamer 188.

In one embodiment there is provided a pharmaceutical composition comprising a compound represented by the formula (1) or its pharmaceutically acceptable salt where the pharmaceutical composition is an oil-in-water emulsion comprising squalene as an oil component, L-α-phosphatidylcholine and Poloxamer 188.

In one embodiment there is provided a pharmaceutical composition comprising a compound represented by the formula (1) or its pharmaceutically acceptable salt where the pharmaceutical composition is an oil-in-water emulsion comprising 0.1-10% w/w squalene as an oil component, 0.01-5% w/w L-α-phosphatidylcholine and 0.01-5% w/w Poloxamer 188.

In one embodiment there is provided a pharmaceutical composition comprising a compound represented by the formula (1) or its pharmaceutically acceptable salt where the pharmaceutical composition is an oil-in-water emulsion comprising 2.5% w/w squalene as an oil component, 0.23% w/w L-α-phosphatidylcholine and 0.05% w/w Poloxamer.

In any embodiment the pharmaceutical composition further comprises an antigen. In one embodiment the antigen is a peptide or a protein. In one embodiment the antigen is an antigen derived from a pathogen or is a tumor antigen. In one embodiment the antigen is any of the antigens recited in the present description.

In one embodiment there is provided an oil-in-water emulsion comprising a compound of formula (1) or its pharmaceutically acceptable salt, an aqueous component which is 1×PBS, an oil component which is squalene, Span (Registered Trademark) 85 (Sorbitan Trioleate) and Poloxamer 188.

In one embodiment there is provided an oil-in-water emulsion comprising 0.01-5% w/w of a compound of formula (1) or its pharmaceutically acceptable salt, an aqueous component which is 1×PBS, an oil component which is 2.5% w/w squalene, 0.23% w/w Span (Registered Trademark) 85 (Sorbitan Trioleate) and 0.3% w/w Poloxamer 188.

In one embodiment there is provided an oil-in-water emulsion comprising a compound of formula (1) or its pharmaceutically acceptable salt, an aqueous component which is 1×PBS, an oil component which is squalene, La-phosphatidylcholine and Poloxamer 188.

In one embodiment there is provided an oil-in-water emulsion comprising 0.01-5% w/w of a compound of formula (1) or its pharmaceutically acceptable salt, an aqueous component which is 1×PBS, an oil component which is 2.5% w/w squalene, 0.23% w/w L-α-phosphatidylcholine and 0.05% w/w Poloxamer 188.

In one embodiment there is provided an oil-in-water emulsion comprising 0.01-5% w/w of a compound of formula (1) or its pharmaceutically acceptable salt, an aqueous component which is 1×PBS, an oil component which is 2.5% w/w squalene, 0.23% w/w Span (Registered Trademark) 85 (Sorbitan Trioleate) and 0.3% w/w Poloxamer 188, wherein the mean particle size of the emulsion droplets is 120 nm±10 nm.

In one embodiment there is provided an oil-in-water emulsion comprising 0.01-5% w/w of a compound of formula (1) or its pharmaceutically acceptable salt, an aqueous component which is 1×PBS, an oil component which is 2.5% w/w squalene, 0.23% w/w L-α-phosphatidylcholine and 0.05% w/w Poloxamer 188, wherein the mean particle size of the emulsion droplets is 120 nm±10 nm.

In any embodiment the oil-in-water emulsion comprises an aqueous component which is PBS (phosphate buffered saline solution). In any embodiment, the PBS is 1×PBS.

In any embodiment the oil-in-water emulsion comprises droplets with a mean particle size of the emulsion droplets is 10-1000 nm±10 nm. In any embodiment, the oil-in-water emulsion comprises droplets with a mean particle size of the emulsion droplets is 20-500 nm±10 nm. In any embodiment, the oil-in-water emulsion comprises droplets with a mean particle size of the emulsion droplets is 50-250 nm±10 nm. In any embodiment, the oil-in-water emulsion comprises droplets with a mean particle size of the emulsion droplets is 100-140 nm±10 nm. In any embodiment, the oil-in-water emulsion comprises droplets with a mean particle size of the emulsion droplets is 120 nm±10 nm.

In any embodiment the oil-in-water emulsion further comprises an antigen. In one embodiment the antigen is a peptide or a protein. In one embodiment the antigen is an antigen derived from a pathogen or is a tumor antigen. In one embodiment the antigen is any of the antigens recited in the present description, for example in paragraph [0139] or paragraph [0147].

The compound of formula (1) or its pharmaceutically acceptable salt or pharmaceutical compositions of either can be administered in simultaneous combination with an antigen or in sequential combination with an antigen. The dose of compound of formula (1) or its pharmaceutically acceptable salt is generally 5-5000 mg/m$^2$ (body surface area) for a warm-blooded animal, or the compound of formula (1) or its pharmaceutically acceptable salt can be administered in a unit dose of about 0.1-100 mg/kg, which can be a therapeutically effective amount thereof. The unit dosage form such as tablets, injectable devices and capsules generally contain, for example, 1-250 mg of compound of formula (1). In one embodiment the compound of formula (1) or its pharmaceutically acceptable salt can be administered in a range of 1-50 mg/kg per day. However, the daily dosage can be modified depending on a patient to be treated, a specific administration route, and the severity of a disease to be treated. Thus, each optimized dose can be decided by a practitioner who treats each patient.

As already mentioned, compounds represented by the formula (1) or their pharmaceutically acceptable salts, or pharmaceutical compositions comprising such compounds or salts can be used as vaccine adjuvants to retain or enhance the antigenicity of an antigen.

Such antigens include tumor antigen protein, or tumor antigen peptides derived from a tumor antigen protein (e.g. NY-ESO-1, MAGE-3, WT1 or Her2/neu), a hypervariable region of an antigen, or an antigen protein or its partial peptide derived from a virus or bacteria. Therefore, a compound of the present specification or its pharmaceutically acceptable salt in combination with said antigen can be used as a medicament for treatment or prophylaxis of cancer, or infection of virus or bacteria.

In addition, the compound of the present specification or its pharmaceutically acceptable salt can be used as an adjuvant to assist the immunostimulating activity in other immunological method of treatment. The specific method of treatment includes, for example, an ex vivo and in vivo approach for enhancing the immunogenicity in patients' tumor cell (e.g. the transfection of a cytokine such as interleukin 2, interleukin 4, and granulocyte-macrophage colony-stimulating factor), an approach for lowering the T cell anergy, an approach with transfect immune cell (e.g. cytokine transfect dendritic cell), an approach with cytokine transfect tumor cell line, and an approach for lowering the function of immune suppressor cell (e.g. regulatory T-cell, bone marrow-derived suppressor cell or IDO (indoleamine 2,3-dioxygenase) expression dendritic cell).

The "treat", "treating" or "treatment" used herein means wholly or partially alleviating one or more, or all of symptoms of a disease; or inhibiting or delaying the progress of a disease.

The "prevent", "preventing", or "prevention" used herein includes the primary prevention (i.e., preventing the onset of a disease) and the secondary prevention (i.e., preventing the relapse of a patient whose symptoms were alleviated or whose disease was healed).

The compound of the present specification or its pharmaceutically acceptable salt, which has an immunologic adjuvant activity in vitro or in vivo, is useful as a vaccine adjuvant. The immunologic adjuvant activity includes induction of antibody production, activation of lymphocytes, and the like.

The compound of the present specification or its pharmaceutically acceptable salt is used to retain or enhance the immunostimulating activity of an antigen which is a medicament for treating or preventing a disease. The antigen includes, but not limited thereto, an antigen protein or an antigen peptide (partial peptide) derived from the antigen protein.

More specifically, the compound of the present specification or its pharmaceutically acceptable salt is useful for treating or preventing a cancer through the administration in combination with a tumor antigen protein or a tumor antigen peptide for cancer immunotherapy. The cancer includes, for example, general cancers such as bladder cancer, head and neck cancer, prostate cancer, breast cancer, lung cancer, ovarian cancer, cervical cancer, pancreatic cancer, bowel cancer, colon cancer, colorectal cancer, anogenital cancer, genital cancer, gastric cancer, skin cancer (for example metastatic melanoma), liver cancer and brain tumor; and malignant diseases affecting bone marrow (including leukemia) and lymphotrophic system such as Hodgkin's lymphoma or non-Hodgkin's lymphoma or Burkitt's lymphoma. The treatment or prevention of cancer therein includes the prevention of metastatic disease and tumor recurrence, and the prevention and treatment of paraneoplastic syndrome.

Therefore, in any embodiment where cancer or tumours are mentioned in a general sense, the cancer or tumor may be any of the conditions listed in the preceding paragraph.

The specific antigens that may be used in such therapy include, for example, MAGE (Science, 254: p1643 (1991)), gp100 (J. Exp. Med., 179: p1005 (1994)), MART-1 (Proc. Natl. Acad. Sci. USA, 91: p3515 (1994)), tyrosinase (J. Exp. Med., 178: p489 (1993)), MAGE-related proteins (J. Exp. Med., 179: p921 (1994)), β-catenin (J. Exp. Med., 183: p1185 (1996)), CDK4 (Science, 269: p1281 (1995)), HER2/neu (J. Exp. Med., 181: p2109 (1995)), mutant-type p53 (Proc. Natl. Acad. Sci. USA, 93: p14704 (1996)), CEA (J. Natl. Cancer. Inst., 87: p982 (1995)), PSA (J. Natl. Cancer. Inst., 89: p293 (1997)), WT1 (Proc. Natl. Acad. Sci. USA, 101: p13885 (2004)), an antigen derived from HPV (J. Immunol., 154: p5934 (1995)), MUC-1, HPV-E6, HPV-E7, HBsAg, HBcAg, Trp1, Trp2, EBV-gp350 and an antigen derived from EBV (Int. Immunol., 7: p653 (1995)).

The tumor antigen peptide derived from a cancer antigen includes, for example, MAGEA3 peptide 168-176 (Coulie P G et al., Immunol. Rev. 188: 33 (2002)), gp100 peptide 209-217 (Rosenberg S A et al., Nat. Med. 4: 321 (1998)), gp100 peptide 280-288 (Phan G Q et al., Proc. Natl. Acad. Sci. USA 100: 8372 (2003)), Melan-A peptide 27-35 (Cormier J N et al., Cancer J. Sci. Am. 3: 37 (1997)), Melan-A peptide 26-35, Tyrosinase peptide 1-9, Tyrosinase peptide 368-376, gp100 peptide 280-288, gp100 peptide 457-466 (Jager E et al., Int. J. Cancer 67: 54 (1996)), HER-2 peptide 369-384, HER-2 peptide 688-703, HER-2 peptide 971-984 (Knutson K L et al., J. Clin. Invest. 107: 477 (2001)), and MAGE-A12 peptide 170-178 (Bettinotti M P et al., Int. J. Cancer 105: 210 (2003)).

In addition, the compound of the present specification or its pharmaceutically acceptable salt can be administered in combination with an active ingredient of a therapeutic or prophylactic vaccine for infection to prevent various infections, for example, a virus disease such as genital wart, verruca vulgaris, plantar wart, hepatitis B, hepatitis C, herpes simplex virus, molluscum contagiosum, smallpox, human immunodeficiency virus (HIV), human papillomavirus (HPV), cytomegalovirus (CMV), varicella-zoster virus (VZV), rhinovirus, Epstein-Ban Virus (EBV) mediated disease, adenovirus, coronavirus, influenza, and parainfluenza; a bacterial disease such as tuberculosis, *Mycobacterium avium, Staphylococcus aureus* infection and leprosy; a fungal infection, *Chlamydia, Candida, Aspergillus*, cryptococcal meningitis, *Pneumocystis carinii*, cryptosporidiosis, histoplasmosis, toxoplasmosis, trypanosomiasis, malaria and leishmaniasis. The active ingredient of a preventive vaccine for infection includes substances derived from microorganism/pathogens such as bacteria, fungi, protozoa, and viruses which cause infections, for example, an antigenic protein, an antigenic peptide (partial peptide) derived from the protein, polysaccharide, lipids and complex thereof.

The antigen peptide derived from a virus includes, for example, influenza matrix protein peptide 58-66 (Jager E et al., Int. J. Cancer 67: 54 (1996)), HPV16 E7 peptide 86-93 (van Driel W J et al., Eur. J. Cancer 35: 946 (1999)), HPV E7 peptide 12-20 (Scheibenbogen C et al., J. Immunother. 23: 275 (2000)), HPV16 E7 peptide 11-20 (Smith J W I et al., J. Clin. Oncol. 21: 1562 (2003)), HSV2 gD (Berman P W et al., Science 227:1490(1985)), CMV gB (Frey S E et al., Infect Dis. 180:1700(1999), Gonczol E. et al., Exp. Opin. Biol. Ther. 1:401(2001)), CMV pp65 (Rosa C L et al., Blood 100:3681(2002), Gonczol E. et al., Exp. Opin. Biol. Ther. 1:401(2001)) and the like.

The antigen peptide can be prepared by synthesis or cloning cDNA to encode an antigen peptide and then expressing it in a host cell, according to a standard text book such as Molecular Cloning 2nd Edt., and Cold Spring Harbor Laboratory Press (1989).

The antigen peptide can be synthesized according to a conventional method used in general peptide chemistry. The synthetic method is described, for example, in a reference such as Peptide Synthesis, Interscience, New York, 1966; and The Proteins, Vol. 2, Academic Press Inc., New York, 1976.

Therefore, in one embodiment there is provided a compound of formula (1) or its pharmaceutically acceptable salt for use in therapy.

In one embodiment there is provided a compound of formula (1) or its pharmaceutically acceptable salt for use in the treatment or prevention of cancer.

In one embodiment there is provided a compound of formula (1) or its pharmaceutically acceptable salt for use in the treatment of cancer.

In one embodiment there is provided a compound of formula (1) or its pharmaceutically acceptable salt for use in the prevention of cancer.

In one embodiment there is provided a compound of formula (1) or its pharmaceutically acceptable salt for use in the treatment or prevention of cancer where the cancer is selected from metastatic melanoma, cervical cancer, head and neck cancer, prostate cancer, lung cancer and liver cancer.

In a further embodiment there is provided a kit comprising:

(a) a compound of formula (1) or its pharmaceutically acceptable salt;

(b) an antigen;

(c) a container or device which can contain each administration-unit of (a) and (b) in combination or in separation; and optionally (d) Instructions for use.

The antigen includes, but not limited thereto as long as it is an antigen used as an active ingredient of vaccine, the above-mentioned protein or an antigen peptide (partial peptide) derived from the protein.

In one embodiment, there is provided a use of a compound of formula (1) or its pharmaceutically acceptable salt for the manufacture of a vaccine adjuvant.

In another embodiment, there is provided a use of a compound of formula (1) or its pharmaceutically acceptable salt as a vaccine adjuvant for the manufacture of a vaccine for treating or preventing a disease or a condition.

In one embodiment, there is provided a method of the treatment or prevention comprising a step of administering an effective amount of a compound of formula (1) or its pharmaceutically acceptable salt with an immunostimulating substance to a patient in need thereof.

EXAMPLES

Hereinafter, the present specification is further illustrated by Examples, but should not be construed to be limited thereto.

Abbreviations

THF: tetrahydrofuran
EtOAc: ethyl acetate
NMP: N-methylpyrrolidinone
TEA: triethylamine

Example 1

6-amino-2-butoxy-9-[4-({[(4E,8E,12E,16E,20E)-4,8,12,17,21,25-hexamethylhexacosa-4,8,12,16,20,24-hexaen-1-yl](methyl)amino}methyl)benzyl]-7,9-dihydro-8H-purin-8-one

[Chem.35]

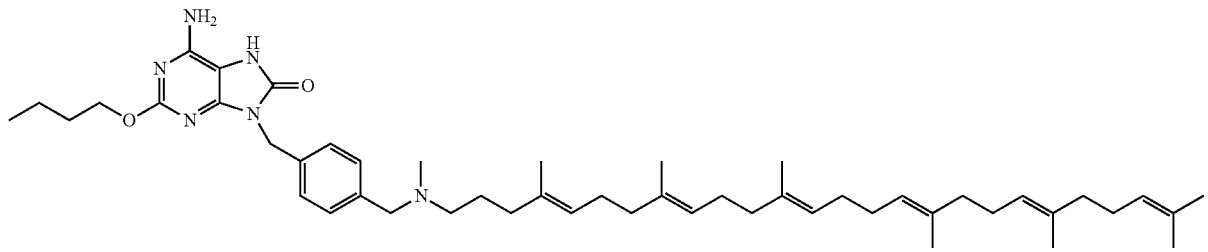

Step 1

[Chem.36]

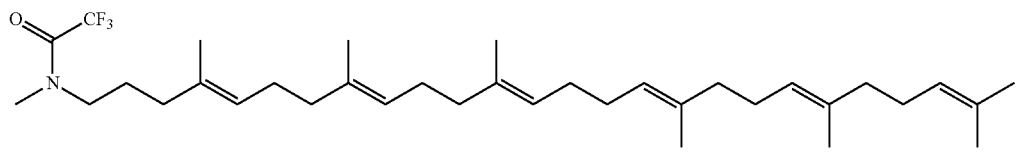

To a solution of (4E,8E,12E,16E,20E)-4,9,13,16,20,25-hexamethylhexacosa-4,8,12,16,20,24-hexen-1-amine (492 mg) in THF at 0° C. was added trifluoroacetic anhydride (0.27 ml), and then the mixture was warmed to room temperature and stirred overnight. The reaction solution was concentrated in vacuo, and EtOAc was added to the residue. The EtOAc solution was washed with saturated aqueous ammonium chloride and brine, and then dried over sodium sulfate. The sodium sulfate was removed out from the solution, and then the solution was concentrated to give an oily product. To the oily product were added cesium carbonate (710 mg), THF (20 ml), and further methyl iodide (0.45 ml), and the mixture was stirred overnight. EtOAc was added to the reaction mixture, and the mixture was washed with saturated aqueous ammonium chloride and brine, and then dried over sodium sulfate. The sodium sulfate was removed out from the solution, and then the solution was concentrated to give a white oily product. The white oily product was purified by silica gel column chromatography (Hexane/EtOAc=7/1) to give the desired compound (421 mg).

$^1$H NMR (400 MHz, CDCl$_3$) δ 5.08-5.18 (m, 6H), 3.30-3.40 (m, 2H), 2.99-3.09 (m, 3H), 1.98-2.10 (m, 22H), 1.52-1.71 (m, 23H).

Step 2

[Chem.37]

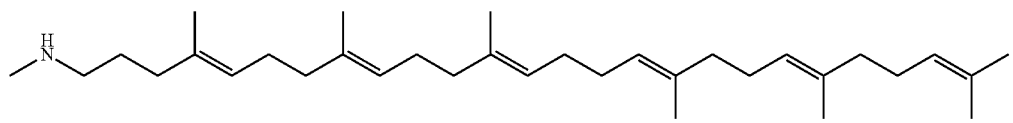

To the compound prepared in Step 1 (175 mg) were added methanol (2 ml), water (0.5 ml), and potassium carbonate (257 mg), and the mixture was stirred at room temperature for 2.5 hours. Water was added to the reaction mixture, and the mixture was extracted with chloroform. The organic layer was washed with brine, dried over sodium sulfate, and then concentrated in vacuo to give the desired compound (146 mg).

$^1$H NMR (400 MHz, CDCl$_3$) δ 5.07-5.12 (m, 6H), 2.52-2.56 (m, 2H), 2.42 (s, 3H), 1.90-2.13 (m, 22H), 1.52-1.72 (m, 23H).

Step 3

[Chem.38]

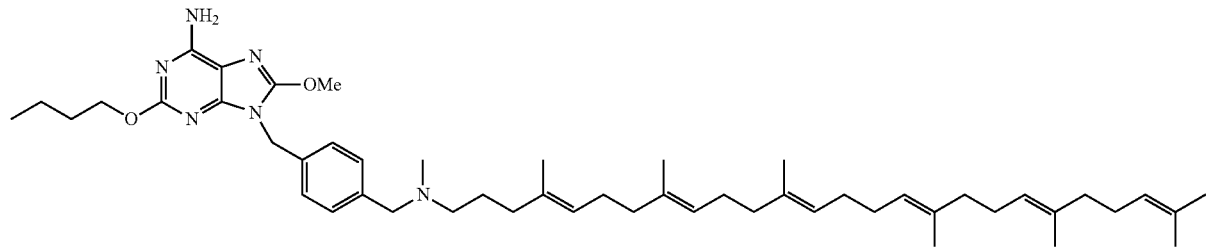

According to the method described in WO2007/034817, (4-((6-amino-2-butoxy-8-methoxy-9H-purin-9-yl)methyl)-phenyl)methanol was prepared, 72 mg of the compound was dissolved in NMP (2.0 ml), and the solution was cooled at 0° C. TEA (0.06 ml) was added thereto, and then an excessive amount of methanesulfonyl chloride (0.05 ml) was added dropwise thereto. The mixture was warmed to room temperature and stirred overnight. EtOAc was added to the reaction mixture, and then the mixture was washed with saturated aqueous ammonium chloride and brine. The organic layer was dried over sodium sulfate. The sodium sulfate was removed out from the solution, and then the solution was concentrated to give a white amorphous product. The product was roughly purified by silica gel column chromatography (CHCl$_3$/MeOH=10/1). The resulting oily product was dissolved in NMP (1.5 ml) and cooled to 0° C. To the solution was added the oily product prepared in Step 2 (102 mg), and then the mixture was warmed to room temperature and stirred overnight. EtOAc was added to the reaction mixture, and then the mixture was washed with saturated aqueous ammonium chloride and brine. The organic layer was dried over sodium sulfate. The sodium sulfate was removed out from the solution, and then the solution was concentrated. The residue was purified by silica gel column chromatography (CHCl$_3$/MeOH=10/1) to give the desired compound, i.e., 2-butoxy-9-[[4-[[[(4E,8E,12E,16E,20E)-4,8,12,17,21,25-hexamethylhexacosa-4,8,12,16,20,24-hexaenyl]-methyl-amino]methyl]phenyl]methyl]-8-methoxy-purin-6-amine (101 mg).

Mass Analysis (LC/MS) Condition

MS: detector Perkin-Elmer Sciex API 150EX Mass spectrometer (40 eV)

HPLC: Shimadzu LC 10ATVP

Column: Shiseido CAPCELL PAK C18 ACR (S-5 µm, 4.6 mm×50 mm)

Solvent A: 0.035% TFA/CH$_3$CN

Solvent B: 0.05% TFA/H$_2$O

Flow rate: 3.5 ml/min

Detector: UV 254, 220 nm

Gradient: 0.0-0.5 min Solvent A 80%, 0.5-4.8 min Solvent A linear gradient from 80 to 99%, 4.8-5.0 min Solvent A 99%

Mass analysis (LC/MS): 1.46 min; [M+H]$^+$=807.9 (Calc.: 807.6)

Step 4

[Chem.39]

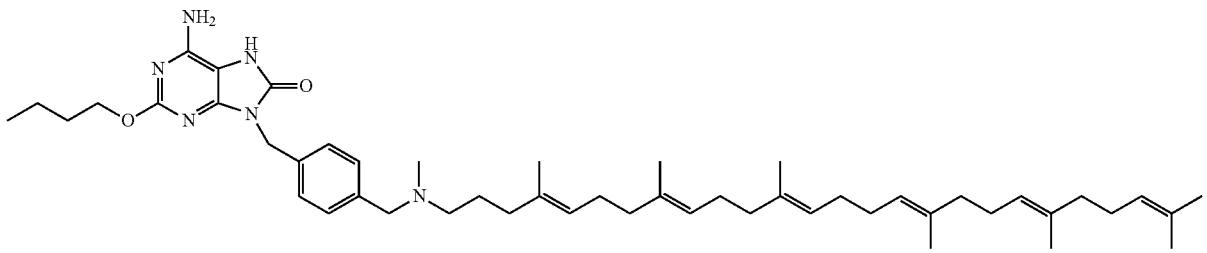

The compound prepared in Step 3, 2-butoxy-9-[4-({[(4E,8E,12E,16E,20E)-4,8,12,17,21,25-hexamethylhexacosa-4,8,12,16,20,24-hexaen-1-yl](methyl)amino}methyl)benzyl]-8-methoxy-9H-purin-6-amine (105 mg) was dissolved in chloroform (1.0 ml), and 5-10% hydrochloric acid/methanol (6.0 ml) was added thereto. The mixture was stirred at room temperature for an hour, and then concentrated. Chloroform was added to the residue, and the chloroform solution was washed with water under a basic condition. The organic layer was dried over sodium sulfate. The sodium sulfate was removed out with a filter, and then the organic solution was concentrated in vacuo. The residue was roughly purified by silica gel column chromatography (CHCl$_3$/MeOH=10/1)

followed by amino-silica gel column chromatography (CHCl₃/MeOH=10/1) to give the desired compound (67 mg).

HRMS (ESI) exact mass calcd. for $C_{50}H_{76}N_6O_2$: m/z 793.6103 ([M+H]⁻), found: m/z 793.6102 ([M+H]+).

¹H NMR (400 MHz, CDCl₃) δ 10.6 (br, 1H), 7.26-7.32 (m, 4H), 5.52 (s, 2H), 5.08-5.18 (m, 6H), 5.02 (s, 2H), 4.26 (t, J=6.6 Hz, 2H), 3.55 (br, 2H), 2.42 (m, 2H), 2.21 (s, 3H), 1.91-2.10 (m, 20H), 1.42-1.80 (m, 29H), 0.95 (t, J=7.3 Hz, 3.0H).

Example 2

Preparation of 6-amino-9-[4-({[(4E,8E,12E,16E,20E)-4,8,12,17,21,25-hexamethylhexacosa-4,8,12,16,20,24-hexaen-1-yl](methyl)amino}methyl)benzyl]-2-(2-methoxyethoxy)-7,9-dihydro-8H-purin-8-one 3 in Example 1 using (4-((6-amino-8-methoxy-2-(2-methoxyethoxy)-9H-purin-9-yl)methyl)phenyl)methanol (70 mg) as a starting material (yield: 71 mg).

Mass Analysis (UPLC/MS) Condition

UPLC/MS: ACQUITY UltraPerfomance LC-PDA-ELSD-SQD (Waters)

HPLC: ACQUITY UPLC BEH C18 1.7 μm, 2.1×30 mm (Part. No. 186002349)

Column: Shiseido CAPCELL PAK C18 ACR (S-5 μm, 4.6 mm×50 mm)

Solvent A: CH₃CN

Solvent B: 0.05% formic acid/H₂O

Flow rate: 0.8 ml/min

Detector: UV 254, 220 nm

[Chem.40]

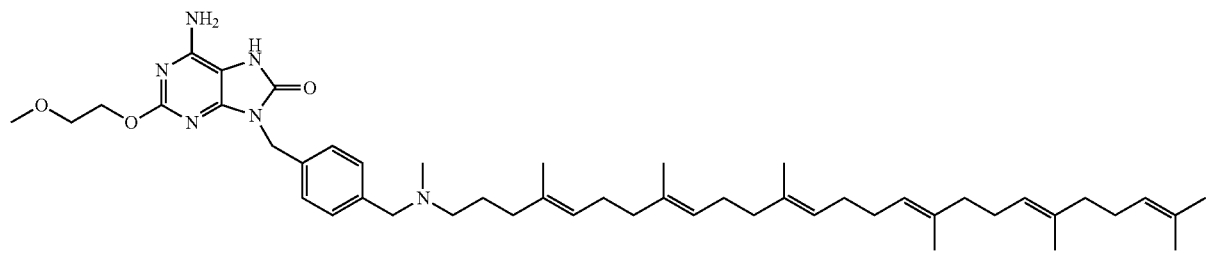

Step 1

[Chem.41]

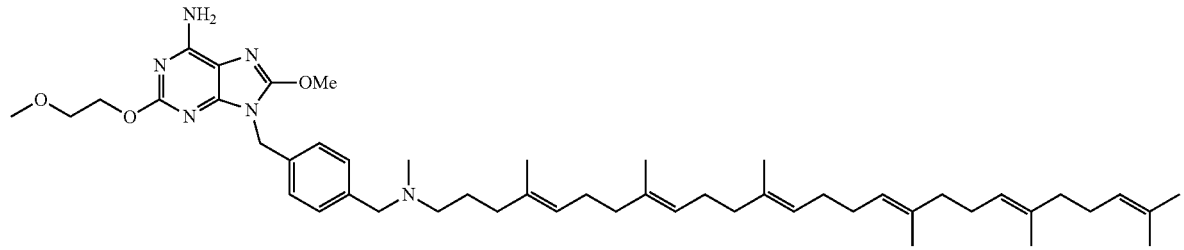

9-[4-({[(4E,8E,12E,16E,20E)-4,8,12,17,21,25-hexamethylhexacosa-4,8,12,16,20,24-hexaen-1-yl](methyl)amino}methyl)benzyl]-8-methoxy-2-(2-methoxyethoxy)-9H-purin-6-amine was prepared in a similar manner to Step Gradient: 0.0-1.3 min Solvent A linear gradient from 60 to 95%

Mass analysis UFLC/MS 0.885 min; [M+H]⁺=809.8 (calc.: 809.6)

Step 2

[Chem.42]

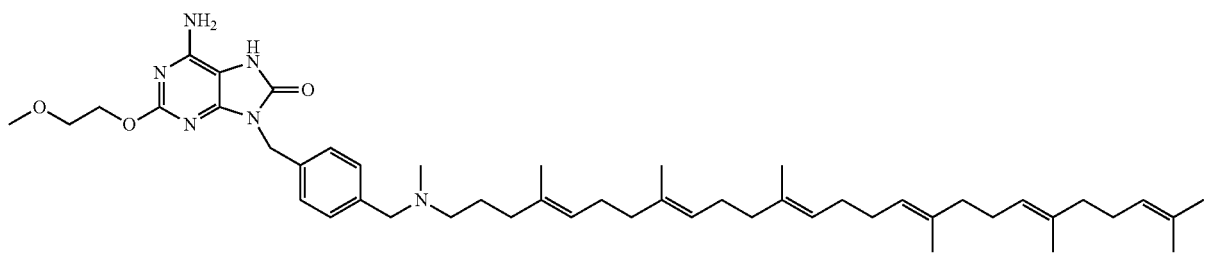

The above desired compound was prepared in a similar manner of Step 4 in Example 1 using the compound (71 mg) of Step 1, i.e. 9-[4-({[[(4E,8E,12E,16E,20E)-4,8,12,17,21,25-hexamethylhexacosa-4,8,12,16,20,24-hexaen-1-yl](methyl)amino}methyl)benzyl]-8-methoxy-2-(2-methoxyethoxy)-9H-purin-6-amine (yield: 49 mg).

HRMS (ESI) exact mass calcd. for $C_{49}H_{74}N_6O_3$: m/z 795.5895 ([M+H]$^+$), found: m/z 795.5895 ([M+H]$^+$).

$^1$H NMR (400 MHz, CDCl$_3$) δ 10.8 (br, 1H), 7.24-7.31 (m, 4H), 5.75 (s, 2H), 5.08-5.18 (m, 6H), 5.02 (s, 2H), 4.44-4.47 (m, 2H), 3.72-3.74 (m, 2H), 3.44 (s, 2H), 3.41 (s, 3H), 2.31-2.36 (m, 2H), 2.14 (s, 3H), 1.90-2.10 (m, 22H), 1.49-1.80 (m, 23H).

Example 3

Preparation of 6-amino-2-(2,3-dihydroxypropoxy)-9-[[4-[[[(4E,8E,12E,16E,20E)-4,8,12,17,21,25-hexamethylhexacosa-4,8,12,16,20,24-hexaenyl]-methylamino]methyl]phenyl]methyl]-7H-purin-8-one To a mixture of 2-chloro-9-(tetrahydro-2H-pyran-2-yl)-9H-purin-6-amine (1.00 g) prepared in a manner described in WO 2012/011606 and (2,2-dimethyl-1,3-dioxolan-4-yl)methanol (5.0 ml) was added sodium hydride (473 mg), and the mixture was stirred at 60° C. for 8 hours. EtOAc was added to the reaction mixture, and then the mixture was washed with saturated aqueous ammonium chloride and brine. The organic layer was dried over sodium sulfate. The sodium sulfate was removed out from the solution, and then the solution was concentrated. The residue was purified by silica gel column chromatography (CHCl$_3$/MeOH=20/1) to give the desired compound (1.43 g).

Mass Analysis (UPLC/MS) Condition
UPLC/MS: ACQUITY UltraPerfomance LC-PDA-ELSD-SQD (Waters)

[Chem.43]

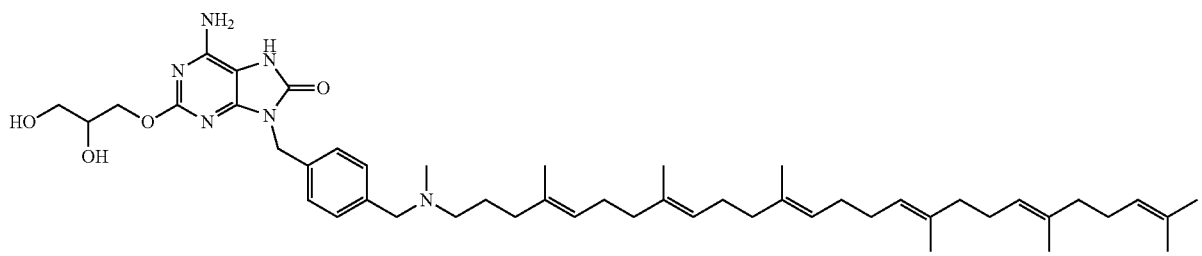

Step 1

[Chem.44]

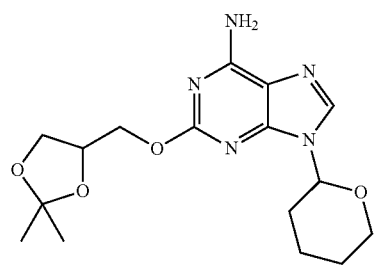

HPLC: ACQUITY UPLC BEH C18 1.7 μm, 2.1×30 mm (Part. No. 186002349)

Column: Shiseido CAPCELL PAK C18 ACR (S-5 μm, 4.6 mm×50 mm)

Solvent A: CH$_3$CN

Solvent B: 0.05% formic acid/H$_2$O

Flow rate: 0.8 ml/min

Detector: UV 254, 220 nm

Gradient: 0.0-1.3 min Solvent A linear gradient from 10 to 95%

Mass analysis UFLC/MS 0.591 min; [M+H]$^+$=350.2 (calc.: 350.2)

Step 2

[Chem.45]

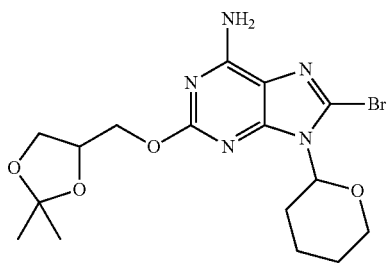

The compound prepared in Step 1 (607 mg) was dissolved in DMF (5.0 ml), and N-bromosuccinimide (325 mg) was added thereto in three portions. The mixture was stirred at room temperature for 30 minutes. EtOAc was added to the reaction mixture, and then the mixture was washed with saturated aqueous ammonium chloride and brine. The organic layer was dried over sodium sulfate. The sodium sulfate was removed out from the solution, and then the solution was concentrated. The residue was purified by silica gel column chromatography ($CHCl_3$/MeOH=10/1) to give the desired compound (419 mg).

Gradient: 0.0-1.3 min Solvent A linear gradient from 10 to 95%

Mass analysis UFLC/MS 0.749 min; $[M+H]^+$=428.3 (calc.: 428.1)

Step 3

[Chem.46]

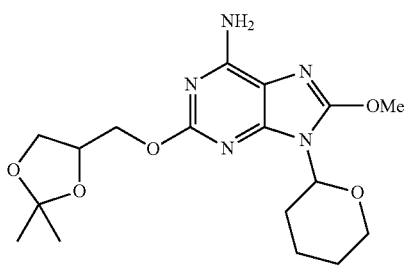

The compound prepared in Step 2 (419 mg) was dissolved in methanol (50 ml), and 2 N aqueous NaOH (15 ml) was added thereto. The mixture was stirred for 8 hours under reflux. The reaction mixture was cooled to room temperature and then the solvent was removed in vacuo. EtOAc was added to the reaction mixture, and then the mixture was washed with saturated aqueous ammonium chloride and brine. The organic layer was dried over sodium sulfate. The sodium sulfate was removed out from the solution, and then the solution was concentrated. The residue was purified by silica gel column chromatography ($CHCl_3$/MeOH=10/1) to give the desired compound (333 mg). Gradient: 0.0-1.3 min Solvent A linear gradient from 10 to 95%

Mass analysis UFLC/MS 0.669 min; $[M+H]^+$=380.3 (calc.: 380.2)

Step 4

[Chem.47]

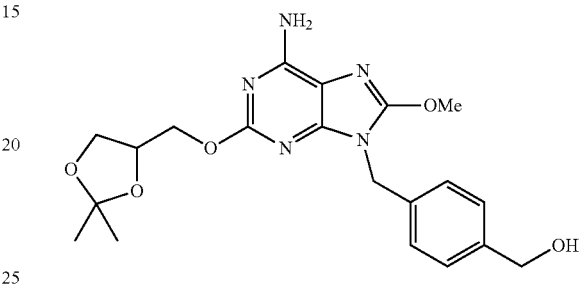

The compound prepared in Step 3 (333 mg) was dissolved in methanol (5.0 ml), and trifluoroacetic acid (3.0 ml) was added thereto. The mixture was stirred at room temperature for 3 hours, and then concentrated. The residue, 0.23 ml of 2,2-dimethoxypropane and a catalytic amount of p-toluenesulfonic acid monohydrate were dissolved in DMF, and the mixture was stirred at room temperature overnight. Then, to the reaction mixture were added potassium carbonate (255 mg) and (4-(chloromethyl)phenyl)methanol (165 mg), and the mixture was stirred overnight. EtOAc was added to the reaction mixture, and then the mixture was washed with saturated aqueous ammonium chloride and brine. The organic layer was dried over sodium sulfate. The sodium sulfate was removed out from the solution, and then the solution was concentrated. The residue was purified by silica gel column chromatography ($CHCl_3$/MeOH=10/1) to give the desired compound (80 mg).

Gradient: 0.0-1.3 min Solvent A linear gradient from 10 to 95%

Mass analysis UFLC/MS 0.585 min; $[M+H]^+$=416.3 (calc.: 416.2)

Step 5

[Chem.48]

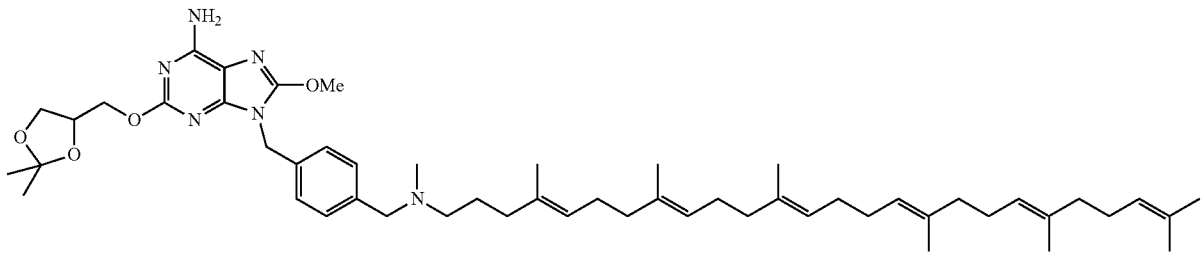

The above desired compound 2-[(2,2-dimethyl-1,3-dioxolan-4-yl)methoxy]-9-[4-({[(4E,8E,12E,16E,20E)-4,8,12,17,21,25-hexamethylhexacosa-4,8,12,16,20,24-hexaen- 1-yl](methyl)amino}methyl)benzyl]-8-methoxy-9H-purin-6-amine was prepared in a similar manner to Step 3 in Example 1 using the compound (81 mg) of Step 4 (yield: 113 mg).

Gradient: 0.0-1.3 min Solvent A linear gradient from 60 to 95%

Mass analysis UFLC/MS 0.950 min; [M+H]⁺=865.8 (calc.: 865.6)

Step 6

[Chem.49]

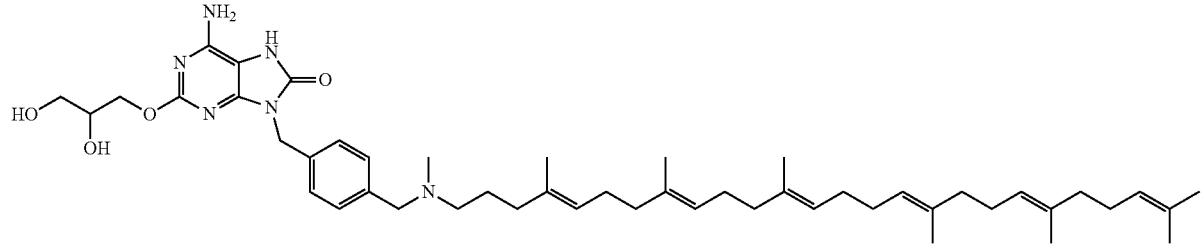

The above desired compound was prepared in a similar manner of Step 4 in Example 1 using the compound (113 mg) prepared in Step 5 (yield: 51 mg).

HRMS (ESI) exact mass calcd. for $C_{49}H_{74}N_6O_4$: m/z 811.5844 ([M+H]⁺), found: m/z 811.5845 ([M+H]⁺).

¹H NMR (400 MHz, CDCl₃-CD₃OD) δ 7.29-7.45 (m, 4H), 5.06-5.20 (m, 6H), 5.00 (s, 2H), 4.30-4.40 (m, 2H), 3.95-4.05 (m, 1H), 3.61-3.74 (m, 4H), 2.20-2.60 (m, 5H), 1.90-2.15 (m, 22H), 1.50-1.80 (m, 23H).

Example 4

Preparation of 6-amino-9-(4-{[(4,8,12,17,21,25-hexamethylhexacosyl)(methyl)amino]methyl}benzyl)-2-(2-methoxyethoxy)-7,9-dihydro-8H-purin-8-one To a solution of (4E,8E,12E,16E,20E)-4,8,12,17,21,25-hexamethylhexacosa-4,8,12,16,20,24-hexaen-1-ol (100 mg) in EtOH (2 ml) was added 10% Pd—C (50% in water)(50 mg) and acetic acid (1 ml), and then the mixture was stirred at room temperature for 7 h under hydrogen atmosphere (0.45 MPa). The reaction mixture was filtered through Celite and the filtrate was concentrated in vacuo. The oily residue was purified by silica gel column chromatography (Hexane/EtOAc=10/1) to give the desired compound (78 mg).

¹H NMR (400 MHz, CDCl₃) δ 3.63 (t, J=6.8 Hz, 2H), 1.65-0.98 (m, 42H), 0.89-0.81 (m, 21H).

[Chem.50]

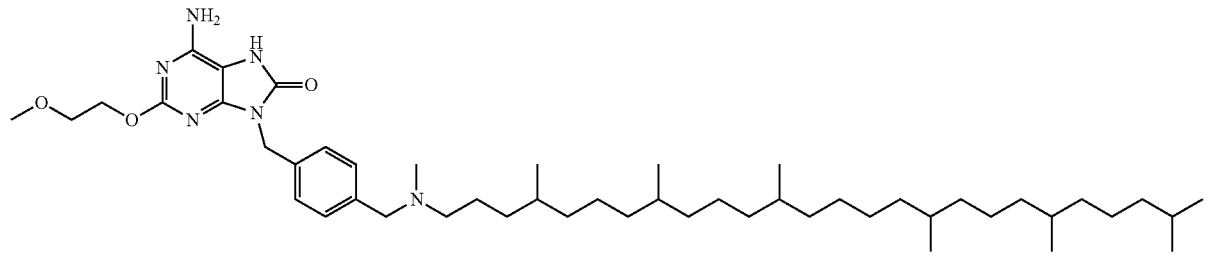

Step 1

[Chem.51]

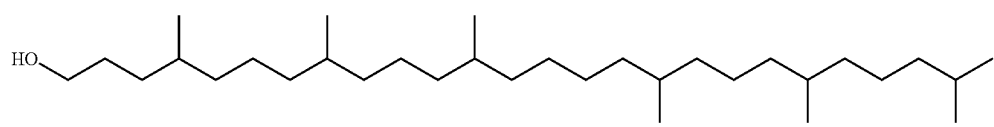

Step 2

[Chem.52]

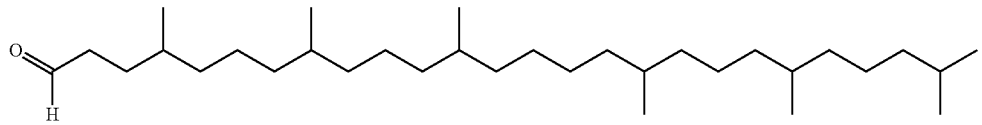

To the compound prepared in Step 1 (200 mg) was added chloroform (4 ml) and Dess-Martin Periodinane (273 mg), and the mixture was stirred at room temperature for 4 hours. Saturated aqueous sodium thiosulfate solution was added to the reaction mixture, and the mixture was extracted with diethyl ether. The organic layer was washed with saturated aqueous sodium hydrogen carbonate solution and brine, dried over sodium sulfate, and then concentrated in vacuo. The oily residue was purified by silica gel column chromatography (Hexane/EtOAc=10/1) to give the desired compound (57 mg).

$^1$H NMR (400 MHz, CDCl$_3$) δ 9.71 (t, J=2.0 Hz, 1H), 2.39-2.30 (m, 2H), 1.66-0.90 (m, 40H), 0.83-0.73 (m, 21H).

Step 3

[Chem.53]

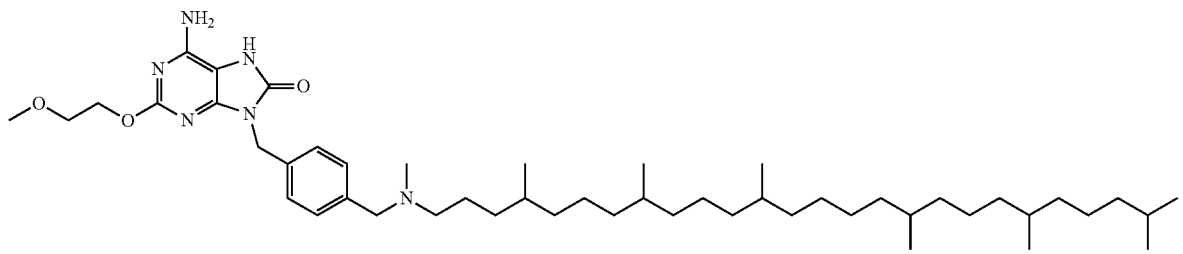

According to the method described in WO2007/034817, 6-amino-2-(2-methoxyethoxy)-9-(4-((methylamino)methyl)benzyl)-7,9-dihydro-8H-purin-8-one was prepared, and 42 mg of the compound and the aldehyde prepared in step 2 (47 mg) was dissolved in chloroform (1 ml). Acetic acid (13 μl) and sodium triacetoxyborohydride (35 mg) was added thereto. The mixture was stirred at room temperature overnight. Water was added to the reaction mixture, and the mixture was extracted with chloroform. The organic layer was washed with brine, dried over sodium sulfate, and then concentrated in vacuo. The residue was purified by silica gel column chromatography (Chloroform/Methanol=10/1) to give the desired compound (25 mg).

$^1$H NMR (400 MHz, CDCl$_3$) δ 7.39-7.28 (m, 4H), 5.56 (s, 2H), 5.00 (s, 2H), 4.45-4.41 (m, 2H), 3.75-3.71 (m, 2H), 3.41 (s, 2H), 3.40 (s, 3H), 2.68-2.55 (m, 2H), 2.41 (s, 3H), 1.70-0.95 (m, 42H), 0.90-0.75 (m, 21H).

Mass Analysis (LC/TOFMS) Condition
MS: detector LCMS-IT-TOF
HPLC: Shimadzu Nexera X2 LC 30AD
Column: Kinetex 1.7 μm C18 100 A New column 50×2.1 mm
Solvent A: 0.1% TFA/H$_2$O
Solvent B: CH$_3$CN
Flow rate: 1.2 ml/min
Detector: UV 254, 220 nm
Gradient: 0.01-1.40 min Solvent B linear gradient from 10 to 95%, 1.40-1.60 min
Solvent B 95%, 161.8-2.00 min Solvent B 99%
ESI: [M+H]$^+$ 807.6

Example 5

Preparation of 6-amino-2-(2-methoxyethoxy)-9-[4-({methyl[(4E,8E,12E,16E)-4,8,13,17,21-pentamethyldocosa-4,8,12,16,20-pentaen-1-yl]amino}methyl)benzyl]-7,9-dihydro-8H-purin-8-one

[Chem.54]

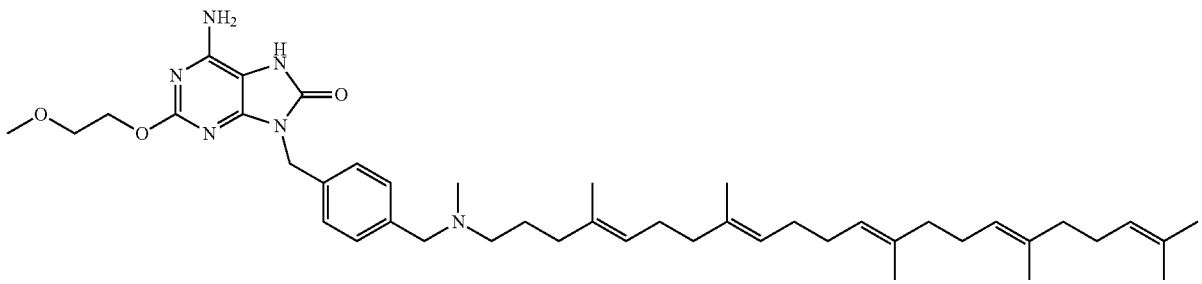

The above desired compound was prepared in a similar manner of Step 3 in Example 4 using 6-amino-2-(2-methoxyethoxy)-9-(4-((methylamino)methyl)benzyl)-7,9-dihydro-8H-purin-8-one (36 mg) and 1,1',2-tris-norsqualene aldehyde (38 mg) prepared by the method described in Org. Biomol. Chem. 2, 1456, (2004) as a starting material (yield: 19 mg).

$^1$H NMR (400 MHz, CDCl$_3$) δ 7.34-7.28 (m, 4H), 5.67 (s, 2H), 5.13-5.04 (m, 5H), 5.00 (s, 2H), 4.45-4.40 (m, 2H), 3.74-3.70 (m, 2H), 3.61 (s, 2H), 3.40 (s, 3H), 2.51-2.46 (m, 2H), 2.26 (s, 3H), 1.90-2.10 (m, 18H), 1.49-1.80 (m, 20H).

Mass Analysis (LC/TOFMS) Condition
MS: detector LCMS-IT-TOF
HPLC: Shimadzu Nexera X2 LC 30AD
Column: Kinetex 1.7 µm C18 100 A New column 50×2.1 mm
Solvent A: 0.1% TFA/H$_2$O
Solvent B: CH$_3$CN
Flow rate: 1.2 ml/min
Detector: UV 254, 220 nm
Gradient: 0.01-1.40 min Solvent B linear gradient from 10 to 95%, 1.40-1.60 min
Solvent B 95%, 161.8-2.00 min Solvent B 99%
ESI: [M+H]$^+$727.4

Several oil-in-water emulsion formulations comprising Examples 1 to 3 were prepared as described in Examples 6 to 9. Note that in FIGS. 1 to 12 showing the activity of these emulsions, Examples 6 to 9 are referred to by their alternative names:
Example 6=ACVT-03;
Example 7=ACVT-01;
Example 8=ACVT-02; and
Example 9=ME7.

Materials and Equipment:
Sonicator from VWR, Symphony;
Mixer from Silverson, model L5M-A;
Microfluidizer from Microfluidics (Registered Trademark), model M110P;
10×PBS from Lonza, P/N 17-517Q, Lot #0000298339 (1×PBS was made by diluting 10×PBS with NanoPure water and filtering through a 0.22 mcm filter);
Span (Registered Trademark) 85 (Sorbitan Trioleate) from Sigma, P/N 57135, Lot # MKBF5282V;
Squalene from Acros, P/N 207471000, Lot # A 0278995;
Poloxamer 188 from Spectrum, P/N P1169, Lot # ZB0478;
NanoPure water.

Analytical Methods:
Dynamic Light Scattering was used to determine the average diameter of micelles in the suspensions. The samples were diluted 100× with water just before taking a measurement.

All of the emulsions prepared herein were determined to have a consistent mean particle size of 120±10 nm.
DLS Instrument: Nano-ZS from Malvern;
SOP used: Size, automated. Three consecutive measurements were taken and the results averaged;
Cuvette Type: Quartz ZEN2112;
Sample diluent: Water for Injection from Thermo, P/N SH30221.10, Lot # AWE10443.

Quantification of TLR7 receptor ligand concentration was achieved using QTOF MassSpec using a standard curve generated by solubilized dry mass of TLR7 receptor ligand. For example, ACVT-2 was prepared as a 4% w/w in formulation buffer. The emulsion was diluted 1:1 with formulation buffer to a working concentration of 2% w/w stable emulsion. The emulsion was then further diluted, serially, to 0.04 and 0.02 mg/mL and all 3 samples were analyzed. Using QTOF-MS, the TLR7 receptor ligand was monitored by its intact mass of 794.58 Daltons. The resulting EIC area plotted against the target concentration generated a fit line with an R$^2$ value of 0.9994, indicating linearity of the samples following serial dilution. The linearity of the fit line supports the claim that the emulsion particles with surface TL7L are uniformly distributed.

Quantification of L-α-phosphatidylcholine and its by-products, poloxamer 188 and squalene oil was carried out using Liquid Chromatography with online Evaporative Light Scattering Detector.

Example 6

"ACVT-03"
Step 1—Preparation of Oil Phase
22 mg of Example 3 was weighed into a screw-cap container and 2.5 g of squalene oil added. Example 3 was then solubilized by sonication at 25° C. for 60 minutes until no particles were visible.

Step 2—Preparation of Aqueous Phase
1×PBS (95 g), Poloxamer 188 (0.3 g) and Span (Registered Trademark) 85 (Sorbitan Trioleate) (0.25 g) were added to a second vessel. The solution was mixed at room temperature for 20 minutes until particle free, and then filtered in a sterile fashion through a 0.2 micron PES or PVDF membrane filter.

Step 3—Preparation of a Continuous Phase Emulsion
The oil and water phases prepared according to steps 1 and 2 were combined in a single vessel and blended. Blending was carried out by ramping up to 9-10,000 RPM and processing for 5 min until the mixture was a continuous phase of milky-white appearance.

Step 4—Microfluidization
The continuous phase emulsion prepared in Step 3 was microfluidized through a Y-type interaction chamber at 25,000-30,000 PSI. After 8 passes the process was determined to be complete. The resulting milky-white liquid was aliquotted into depyrogenated glass vials and stored at 4° C. when not in use.

Example 7

"ACVT-01"
Example 7 was prepared in a similar manner to that described in Example 6, but Example 1 was used as a component in step 1 rather than Example 3.

Example 8

"ACVT-02"
Example 8 was prepared in a similar manner to that described in Example 6, but Example 2 was used as a component in step 1 rather than Example 3.

Example 9

"ME7"
Example 9 was prepared in a similar manner to that described in Example 6, using the following materials:
Surfactants: L-α-phosphatidylcholine (0.8% w/w) (ionic surfactant); Poloxamer 188 (0.05% w/w) (non-ionic linear copolymer)
Oil: Squalene (40 mg/mL)

TLR7 receptor ligand: Example 2 (1 µg/mL-400 µg/mL) L-α-phosphatidylcholine was added to the oil phase before sonication.

The resultant emulsion had the following characteristics:
Particle size: 80-200 nm
Sterile filterable: Yes (Reference Example 10) "ACVT"

To act as a control for the biological experiments described herein, Reference Example 10 was prepared according to the method described in Example 6 but without adding any Example 3 in step 1. Therefore, Reference Example 10 ("ACVT") is an emulsion containing no TLR7 receptor ligand.

(Reference Example 11) "ME0"

To act as a control for the biological experiments described herein, Reference Example 11 was prepared according to the method described in Example 9 but without adding any Example 2 in step 1. Therefore, Reference Example 11 ("ME0") is an emulsion containing no TLR7 receptor ligand.

INDUSTRIAL APPLICABILITY

The compounds of the present specification are expected to be useful as adjuvants for enhancing immunostimulating activity, and can be used as an additive in a vaccine preparation (for example a cancer vaccine preparation) comprising an antigen (such as a tumor antigen peptide) as an active ingredient. The vaccine adjuvant activity of the compounds of the specification is supported by the following biological assays:

a) mouse IFN-γ ELISPOT assay [HSV2 gDt antigen]; b) multifunctional CD4 T cells assayed by FACS Intracellular Staining [HSV2 gDt antigen]; c) antigen-specific IgG, IgG1, IgG2c ELISA [HSV2 gDt antigen]; d) mouse IFN-γ ELISPOT assay [CMV pp65 antigen]; e) multifunctional CD4 T cells assayed by FACS Intracellular Staining [CMV pp65 antigen]; f) antigen-specific IgG, IgG1, IgG2a ELISA [CMV pp65 antigen]; g) in-vivo cytotoxicity.

During the description of the assays, generally:
The following abbreviations have been used: TLR7L=Toll-Like Receptor 7 ligand; i.m.=intramuscular; gDt=glycoprotein D terminal from HSV2 genome; HSV2=herpes simplex virus 2; h=hours; r.t.=room temperature; CpG-B=oligonucleotide containing CG dinucleotide motif(s) of the B class; CpG-C=oligonucleotide containing CG dinucleotide motif(s) of the C class; CFSE=Carboxyfluorescein succinimidyl ester; CMV=cytomegalovirus; pp65=polyprotein 65; v:v=volume for volume Data are representative of 2 to 3 experiments.
Sample Preparation using HSV2 gDt Antigen 8-9 week old CB6F1 mice were immunized i.m. at day 0 and 14 with 10 µg HSV2 gDt (amino acids 25-281) antigen adjuvanted with Examples 6, 7 and 8 ("ACVT-03", "ACVT-01" and "ACVT-02" respectively), 4 mice per group. Examples 6, 7 and 8 were administered such that the dose of TLR7L delivered per mouse was 20 µg (in 100 µl). For comparison purposes, a group of mice were immunized with gDt antigen formulated in 50% v:v AddaVax (InVivogen), a commercially available oil-in-water squalene emulsion equivalent in composition to MF59, the commercially licensed squalene emulsion from Novartis used in the vaccine FLUAD, and 20 µg of the CpG-C oligodeoxynucleotide 2395 (InVivogen). This CpG+AddaVax composition had been previously observed to induce strong T cell responses in mice and was used as a positive control. One group of mice was immunized with Reference Example 10 ("ACVT") mixed simply with Example 2 as a comparison of adjuvant activity between merely mixing a soluble TLR7L with an emulsion and delivering the TLR7L integrated into the oil droplets of the emulsion as prepared by the method of Examples 6 to 8. At day 28, mice were terminally bled and spleens were harvested.

a) Mouse IFN-γ ELISPOT Assay

Splenocytes were stimulated in ELISPOT plates for 24 h with gDt peptides (15-mers overlapping by 11 that span the entire gDt sequence). Spot-forming cells were scanned and analyzed using the CTL ImmunoSpot Analyzer (Cellular Technologies Limited). In FIG. 1, all three of Examples 6 to 8 induced higher IFN-γ responses than the CpG/AddaVax formulation. In FIG. 2, splenocytes were pooled in equal measure between the 4 mice within each group and then bound with anti-CD4 magnetic beads (Miltenyi) and CD4 T cells removed through MACS (magnetic-activated cell sorting) to yield splenocyte populations that were <1.0% $CD4^+$ and therefore contained predominantly CD8 T cells. These cell populations were also used in the ELISPOT assay to detect CD8-specific T cell responses. Two of the formulations that incorporated TLR7L-squalene conjugates, Examples 6 and 8 ("ACVT-03" and "ACVT-02" respectively), induced higher CD8 T cell responses than the CpG/AddaVax formulation or the TLR7L+Reference Example 10 admixture.

b) Multifunctional CD4/8 T Cells Assayed by FACS Intracellular Staining

Splenocytes were pooled in equal measure between the 4 mice within each group, stimulated for 6 h with gDt peptide pool+GolgiPlug (BD Biosciences), then stained for cell surface markers using rat anti-mouse CD3e-BV421, rat anti-mouse CD4 PerCP-Cy5.5, rat anti-mouse CD8a APC-H7 (BD Biosciences) and Live/Dead stainBlue reagent (Invitrogen), followed by fixing with 2% Cytofix (BD Biosciences). Cells were re-suspended in BD Perm Wash permeabilization buffer (BD Biosciences), incubated 30 min at r.t., and then stained with a cocktail containing IFN-γ-APC, IL2-PE, GM-CSF, and TNF-α Alexa 488 (BD Biosciences). Acquisition (100,000 events/sample) was conducted on a BD Biosciences LSR2 cytometer utilizing FACS DIVA Software. Subset and Boolean gating analysis (for multifunctional T cells) was performed using FLOWJO software (TreeStar, Menlo Park, Calif.). In FIG. 3, data are reported as % cytokine-positive subsets within CD4- or CD8-gated T cell populations. All three of Examples 6 to 8 demonstrated equivalent or superior induction of multifunctional CD4 T cells. Although at a lower magnitude than Example 7, the Example 8 adjuvant preparation induced a higher percentage of triple-positive IFN-γ$^+$ TNF-α$^+$ IL2$^+$ CD4 T cells as well as IFN-γ$^+$ TNF-α$^+$ subset. FIG. 4 shows that when gated on the $CD3^+$ $CD8^+$ T cell population, Example 7 induces the highest magnitude response of $CD8^+$ cytokine-expressing cells, although most are only IL-2$^+$, while Example 8 does induce detectable IFN-γ$^+$ IL-2$^+$ and GM-CSF$^+$ IFN-γ$^+$ subsets.

c) Antigen-Specific IgG, IgG1, IgG2c ELISA

Sera were isolated from terminal blood samples at day 28 and then analyzed via ELISA for HSV-gDt-specific immunoglobulins. HSV2-gDt antigen was used to coat ELISA plates followed by incubation with six 1:3 serial dilutions starting from 1:50 of sera samples from individual mice to bind gDt-specific IgG. Biotinylated detection antibodies specific to IgG, IgG1, and IgG2c were then used as second steps, followed by HRP-streptavidin, substrate, and reading at 450 nm on an ELISA plate reader. Examples 7 and 8 induced comparable levels of anti-gDt IgG titers to that of the CpG/AddaVax group (FIG. 5). Both Examples 7 and 8 also induced a higher proportion of IgG2c:IgG1 subtypes than CpG/AddaVax, denoting the induction of a robust Th1 response.

Sample Preparation Using CMV Pp65 Antigen 8-9 week old BALB/c mice were immunized i.m. at day 0 and 14 with 10 µg CMV pp65 antigen adjuvanted with Example 9, 5 mice per group. Example 9 was administered such that the dose of TLR7L delivered per mouse would have been 10 µg (in 100 µl). For comparison purposes, a group of mice were immunized with pp65 antigen formulated in 50% v:v AddaVax (InVivogen), a commercially available oil-in-water squalene emulsion equivalent in composition to MF59, with and without 20 µg of the CpG-C oligodeoxynucleotide 2395 or 20 µg of the CpG-B oligodeoxynucleotide 1826 (both InVivogen). These CpG+AddaVax compositions had been previously observed to induce strong T cell responses in mice and were used for positive controls. One group of mice was immunized with Reference Example 11 ("ME0") mixed with the TLR7L of Example 2 as a comparison of adjuvant activity between merely mixing a soluble TLR7L with an emulsion and delivering the TLR7L as integrated into the oil droplets of the emulsion according to the preparation of Example 9. At day 21, mice were terminally bled and spleens were harvested.

d) Mouse IFN-γ ELISPOT Assay

Splenocytes were stimulated in ELISPOT plates for 24 h with pp65 peptides (15-mers overlapping by 11 that span the entire pp65 sequence). Spot-forming cells were scanned and analyzed using the CTL ImmunoSpot Analyzer (Cellular Technologies Limited). FIG. 6 demonstrates that Example 9 ("ME7") induced higher IFN-γ responses than the CpG/AddaVax formulations. In addition, the simple admixture of soluble TLR7L+Reference Example 11 exerted poor T cell induction responses. Splenocytes were pooled in equal measure between the 5 mice within each group and then bound with anti-CD4 magnetic beads (Miltenyi), and CD4 T cells removed through MACS (magnetic-activated cell sorting) to yield splenocyte populations that were <1.0% CD4$^+$ and therefore contained predominantly CD8 T cells. These cell populations were also used in the ELISPOT assay to detect CD8-specific T cell responses in FIG. 7. Example 9 induced a comparable CD8 T cell response to the CpG/AddaVax formulation and a much higher response than the TLR7L+ Reference Example 11 admixture.

e) Multifunctional CD4/8 T Cells Assayed by FACS Intracellular Staining

Splenocytes were pooled in equal measure between the 5 mice within each group, stimulated for 6 h with pp65 peptide pool+Brefeldin A (BD Biosciences), then stained for cell surface markers using rat anti-mouse CD3e-BV510, rat anti-mouse CD4 APC-Cy7, rat anti-mouse CD8a BV711 (BD Biosciences) and Live/Dead Fixable Blue reagent (Invitrogen), followed by fixing with 2% Cytofix (BD Biosciences). Cells were re-suspended in BD Perm Wash permeabilization buffer (BD Biosciences), incubated 30 min at r.t., and then stained with a cocktail containing IFN-γ-BV605, IL2-PerCP-Cy5.5, and TNF-α-BV421 (BD Biosciences). Acquisition (100,000 events/sample) was conducted on a BD Biosciences LSR2 cytometer utilizing FACS DIVA Software. Subset and Boolean gating analysis (for multifunctional T cells) was performed using FlowJo software (TreeStar, Menlo Park, Calif.). Data are reported in FIG. 8 as % cytokine-positive subsets within CD4- or CD8-gated T cell populations. Example 9 demonstrated superior induction of multifunctional CD4 T cells in comparison to the CpG/AddaVax or TLR7L/Reference Example 11 formulations. When gated on the CD3$^+$ CD8$^+$ T cell population in FIG. 9, Example 9 induces a comparable magnitude response of multifunctional CD8$^+$ cytokine-expressing cells to CpG/AddaVax.

f) Antigen-Specific IgG, IgG1, IgG2c ELISA

Sera were isolated from terminal blood samples at day 21 and then analyzed via ELISA for HSV-gDt-specific immunoglobulins. HSV2-gDt antigen was used to coat ELISA plates followed by incubation with six 1:3 serial dilutions starting from 1:50 of sera samples from individual mice to bind gDt-specific IgG. Biotinylated detection antibodies specific to mouse IgG was then used as a second step, followed by HRP-streptavidin, substrate, and reading at 450 nm on an ELISA plate reader. CpG-C/AddaVax, Reference Example 11, and Example 9 all induced the highest levels of total gDt-specific IgG titers (FIG. 10). Admixture of soluble TLR7L+Reference Example 11 was suboptimal compared to the integrated Example 9 formulation. Sera samples were also analyzed with secondary antibodies specific to the subtypes IgG1 and IgG2a (FIG. 11). Higher IgG2a:IgG1 ratios, indicative of robust Th1 responses, were achieved by CpG/AddaVax and Example 9, but not TLR7L+AddaVax.

g) In Vivo Cytotoxicity Assay

Naive BALB/c splenocytes were used to generate two populations of target cells. One population was loaded with 10 µM CFSE dye and 2 µg/ml pp65 overlapping peptides while the other was loaded with 1 µM CFSE dye and 2 µg/ml EBV gp350 overlapping peptides (from an irrelevant antigen), to provide normalization for pp65-specific effects. Equivalent proportions of both target populations were injected on day 28 via tail vein i.v. route into mice that had been immunized twice (day 0, 14) with 10 µg CMV-pp65 Ag adjuvanted with either 20 µg CpG formulated in 50% v:v AddaVax or with Example 9. Recipient mice were sacrificed 18-24 h later and splenocytes were isolated and then analyzed via flow cytometry for CFSE signal, in which bright and dim CFSE signals were used to distinguish the target populations. pp65-specific target killing was normalized to control gp350-specific target killing by the formula % specific killing=(1−% CFSE$^{hi}$ cells/% CFSE$^{lo}$ cells)×100. FIG. 12 indicates that mice immunized with pp65 adjuvanted with Example 9 demonstrated comparable cytotoxicity of pp65-loaded target cells as did mice immunized with CpG+AddaVax.

The invention claimed is:

1. A compound of formula (1):

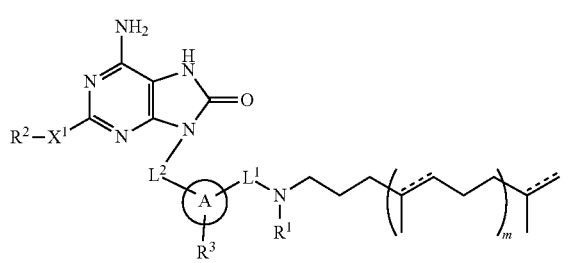

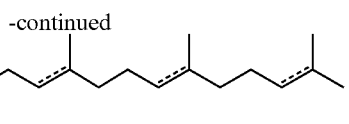

or a pharmaceutically acceptable salt thereof, wherein:
$L^1$ and $L^2$ are independently alkylene;
$R^1$ is hydrogen atom or alkyl;
$R^2$ is optionally substituted alkyl;
$R^3$ is hydrogen atom, halogen atom, alkyl or alkoxy;
$X^1$ is single bond, oxygen atom, sulfur atom, SO, $SO_2$, $NR^4$ or $CONR^4$;
$R^4$ is hydrogen atom or alkyl;
A is a monocyclic aromatic carbocycle, a 5-membered aromatic heterocycle which includes 1 to 2 heteroatoms selected from the group consisting of 1 to 2 nitrogen atoms, an oxygen atom, and a sulfur atom, or a 6-membered aromatic heterocycle which includes 1 to 3 heteroatoms selected from the group consisting of 1 to 3 nitrogen atoms, an oxygen atom, and a sulfur atom;
m is 0 or 1; and
each bond described by

===== independently represents a single bond or a double bond.

2. The compound according to claim 1, or a pharmaceutically acceptable salt thereof, wherein
$L^1$ is $C_{1-4}$ alkylene;
$L^2$ is $C_{1-4}$ alkylene;
$R^1$ is hydrogen atom or $C_{1-4}$ alkyl;
$R^2$ is $C_{1-6}$ alkyl optionally substituted by 1 to 4 groups that may be the same or different selected from hydroxy, halogen atom, $C_{1-6}$ alkyl, $C_{1-6}$ haloalkyl, $C_{1-6}$ alkoxy, $C_{1-6}$ haloalkoxy, amino optionally substituted by one or two $C_{1-6}$ alkyl that may be the same or different, and carboxy;
$R^3$ is hydrogen atom, halogen atom, $C_{1-4}$ alkyl or $C_{1-4}$ alkoxy;
$X^1$ is single bond, oxygen atom, sulfur atom, SO, $SO_2$, $NR^4$ or $CONR^4$; and
$R^4$ is hydrogen atom or $C_{1-4}$ alkyl.

3. The compound according to claim 1, or a pharmaceutically acceptable salt thereof, wherein $R^2$ is $C_{1-6}$ alkyl optionally substituted by 1 to 3 groups that may be the same or different selected from hydroxy, halogen atom, $C_{1-6}$ alkoxy and $C_{1-6}$ haloalkoxy.

4. The compound according to claim 1, or a pharmaceutically acceptable salt thereof, wherein A is benzene ring or pyridine ring.

5. The compound according to claim 4, or a pharmaceutically acceptable salt thereof, wherein A is benzene ring.

6. The compound according to claim 1, or a pharmaceutically acceptable salt thereof, wherein $L^2$ is methylene.

7. The compound according to claim 1, or a pharmaceutically acceptable salt thereof, wherein $R^2$ is $C_{1-4}$ alkyl, $C_{1-4}$ hydroxy-alkyl, or $C_{1-4}$ alkoxy-$C_{1-4}$ alkyl.

8. The compound according to claim 1, or a pharmaceutically acceptable salt thereof, wherein $L^1$ is $C_{1-3}$ alkylene, and $R^1$ is hydrogen atom or $C_{1-3}$ alkyl.

9. The compound according to claim 1, or a pharmaceutically acceptable salt thereof, wherein all of the bonds described by

===== represent a single bond, or all of the bonds described by

===== represent a double bond.

10. The compound according to claim 1, or a pharmaceutically acceptable salt thereof, wherein $R^1$ is hydrogen atom or methyl.

11. The compound according to claim 1, or a pharmaceutically acceptable salt thereof, wherein
$L^1$ is methylene;
$L^2$ is methylene;
$R^1$ is hydrogen atom or methyl;
$R^2$ is $C_{1-6}$ alkyl, $C_{1-3}$ alkoxy-$C_{2-4}$ alkyl or $C_{2-6}$ alkyl substituted by 1 to 4 hydroxy groups wherein two or more hydroxy groups are attached to different carbon atoms;
$R^3$ is hydrogen atom, $C_{1-3}$ alkyl, $C_{1-3}$ alkoxy, or halogen atom;
$X^1$ is single bond, oxygen atom, $NR^4$ or $CONR^4$;
$R^4$ is hydrogen atom or $C_{1-3}$ alkyl;
A is benzene ring or pyridine ring; and
all of the bonds described by

===== represent a single bond, or all of the bonds described by

===== represent a double bond.

12. A pharmaceutical composition comprising a compound according to claim 1, or a pharmaceutically acceptable salt thereof, and one or more pharmaceutically acceptable diluents or carriers.

13. The pharmaceutical composition according to claim 12 wherein the pharmaceutical composition is an oil-in-water emulsion comprising squalene, and one or more surfactants selected from the group consisting of Sorbitan Trioleate, Poloxamer 188, and L-α-phosphatidylcholine.

14. The pharmaceutical composition according to claim 13 wherein the pharmaceutical composition comprises:
a) squalene, Sorbitan Trioleate, and Poloxamer 188; or
b) squalene, L-α-phosphatidylcholine, and Poloxamer 188.

15. The pharmaceutical composition according to claim 13 wherein the oil-in-water emulsion comprises droplets with a mean particle size of 10-1000 nm±10 nm.

16. The pharmaceutical composition according to claim 12 further comprising an antigen.

17. The pharmaceutical composition according to claim 16, wherein the antigen is an antigen derived from a pathogen or is a tumor antigen.

18. The pharmaceutical composition according to claim 16, wherein the antigen is a peptide or a protein.

19. A method of retaining or enhancing an immunostimulating activity of an antigen comprising administering an effective amount of a compound according to claim 1, or a pharmaceutically acceptable salt thereof, to a mammal in need thereof.

20. The method of claim 19 wherein the compound activates a Toll-like Receptor.

21. The method of claim 19 wherein the compound activates one or both of TLR 7 and TLR 8.

22. The compound according to claim 1 wherein the compound of formula (1) is selected from the group consisting of 6-amino-2-butoxy-9-[4-({[(4E,8E,12E,16E,20E)-4,8,12,17,21,25-hexamethylhexacosa-4,8,12,16,20,24-hexaen-1-yl](methyl)amino}methyl)benzyl]-9H-purin-8-ol; 6-amino-9-[4-({[(4E,8E,12E,16E,20E)-4,8,12,17,21,25-hexamethylhexacosa-4,8,12,16,20,24-hexaen-1-yl](methyl)amino}methyl)benzyl]-2-(2-methoxyethoxy)-9H-purin-8-ol; and 3-({6-amino-9-[4-({[(4E,8E,12E,16E,20E)-4,8,12,17,21,25-hexamethylhexacosa-4,8,12,16,20,24-hexaen-1- yl](methyl)amino}methyl)benzyl]-8-hydroxy-9H-purin-2-yl}-oxy)propane-1,2-diol; or a pharmaceutically acceptable salt thereof.

23. The pharmaceutical composition according to claim 12 wherein the compound of formula (1) is selected from the group consisting of 6-amino-2-butoxy-9-[4-({[(4E,8E,12E,16E,20E)-4,8,12,17,21,25-hexamethylhexacosa-4,8,12,16,20,24-hexaen-1-yl](methyl)amino}methyl)benzyl]-9H-purin-8-ol; 6-amino-9-[4-({[(4E,8E,12E,16E,20E)-4,8,12,17,21,25-hexamethylhexacosa-4,8,12,16,20,24-hexaen-1-yl](methyl)amino}methyl)benzyl]-2-(2-methoxyethoxy)-9H-purin-8-ol; and 3-({6-amino-9-[4-({[(4E,8E,12E,16E,20E)-4,8,12,17,21,25-hexamethylhexacosa-4,8,12,16,20,24-hexaen-1-yl](methyl)amino}methyl)benzyl]-8-hydroxy-9H-purin-2-yl}-oxy)propane-1,2-diol; or a pharmaceutically acceptable salt thereof.

24. A method of enhancing immunostimulating activity of an antigen, comprising a step of administering an effective amount of a compound according to claim 1, or a pharmaceutically acceptable salt thereof, to a mammal in need thereof.

25. The method according to claim 19, wherein the antigen is an antigen derived from a pathogen or is a tumor antigen.

26. The method according to claim 19, wherein the antigen is a peptide or a protein.

\* \* \* \* \*